United States Patent
George et al.

(10) Patent No.: US 10,376,173 B2
(45) Date of Patent: Aug. 13, 2019

(54) DETECTION AND ANALYSIS OF CARDIAC WAVEFORMS

(71) Applicant: CARDIOINSIGHT TECHNOLOGIES, INC., Independence, OH (US)

(72) Inventors: Brian P. George, Cleveland, OH (US); Meredith E. Stone, Strongsville, OH (US); Qingguo Zeng, Solon, OH (US); Qing Lou, Powell, OH (US); Connor S. Edel, Independence, OH (US); Ping Jia, Solon, OH (US); Jeffrey B. Adair, Cuyahoga Falls, OH (US); Vladimir A. Turovskiy, Strongsville, OH (US); Matthew J. Sabo, Independence, OH (US); Ryan M. Bokan, Cleveland, OH (US); Ketal C. Patel, Independence, OH (US); Charulatha Ramanathan, Solon, OH (US); John E. Anderson, Chagrin Falls, OH (US); Andrew E. Hoover, Independence, OH (US); Cheng Yao, Independence, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 149 days.

(21) Appl. No.: 15/498,719

(22) Filed: Apr. 27, 2017

(65) Prior Publication Data

US 2017/0319088 A1 Nov. 9, 2017

Related U.S. Application Data

(60) Provisional application No. 62/331,103, filed on May 3, 2016.

(51) Int. Cl.
*A61B 5/00* (2006.01)
*A61B 5/0456* (2006.01)
(Continued)

(52) U.S. Cl.
CPC ........ *A61B 5/0456* (2013.01); *A61B 5/04014* (2013.01); *A61B 5/04017* (2013.01);
(Continued)

(58) Field of Classification Search
CPC .................. A61B 5/0456; A61B 5/04014
(Continued)

(56) References Cited

U.S. PATENT DOCUMENTS

2004/0243192 A1* 12/2004 Hepp ................ A61N 1/36585
607/17
2005/0113705 A1   5/2005  Fischell
2015/0164349 A1   6/2015  Gopalakrishnan

FOREIGN PATENT DOCUMENTS

EP   1484083        12/2004
WO   20140121106    8/2014

OTHER PUBLICATIONS

C. Meyer, et al,; "Combining Algortihms in Automatic Detection of QRS Complexes in ECG Signals", IEEE Transactions on Information Technology in Biomedicine, vol. 10, No. 3, Jun. 5, 2006, pp. 468-475, XP055390082.

(Continued)

*Primary Examiner* — Nadia A Mahmood
(74) *Attorney, Agent, or Firm* — Tarolli, Sundheim, Covell & Tummino

(57) ABSTRACT

An example method includes performing amplitude-based detection to determine location of R-peaks for a plurality of electrograms. The method also includes performing wavelet-based detection to determine location of R-peaks for the plurality of electrograms. The method also includes adjust- (Continued)

ing the location of the R-peaks determined by the wavelet-based detection of R-peaks based on the location of R-peaks determined by the amplitude-based detection of R-peaks. The method also includes storing, in memory, R-peak location data to specify R-peak locations for the plurality of electrograms based on the adjusting.

23 Claims, 23 Drawing Sheets

(51) Int. Cl.
    *A61B 5/04*     (2006.01)
    *A61B 5/0408*     (2006.01)
    *A61B 5/0452*     (2006.01)
(52) U.S. Cl.
    CPC ...... *A61B 5/04085* (2013.01); *A61B 5/04525* (2013.01); *A61B 5/7203* (2013.01); *A61B 5/726* (2013.01)
(58) Field of Classification Search
    USPC .......................................... 600/521
    See application file for complete search history.

(56) References Cited

OTHER PUBLICATIONS

Christov Ivaylo I: "Real Time Electrocardiogram QRS Detection Using Combined Adaptive Threshold", Biomedical Engineering Online, Biomed Central Ltd, London, GB, vol. 3,M No. 1, Aug. 27, 2004, p. 28, XP021007742.

Choi S, et al.: "Development of ECG Beat Segmentation Method by Combining Lowpass Filter and Irregular R@?R Interval Checkup Strategy", Expert Systems With Applications, Oxford, GB, vol. 37, No. 7, Jul. 1, 2010, pp. 5208-5218, XP026989070.

Alavi Saeed, et al:, "A New Combinatorial Algorithm for QRS Detection", ICCKE 2013, IEEE, Oct. 31, 2013, pp. 396-399, XP032531139.

Jiapu Pan, et al.; "A Real-Time QRS Detection Algorithm"; IEEE Transactions on Biomedical Engineering, vol. BME-32, No. 3, Mar. 1, 1985, pp. 230-236, XP055129317.

International Search Report with Written Opinion for Application No. PCT/US2017/029324, dated Jul. 19, 2017.

* cited by examiner

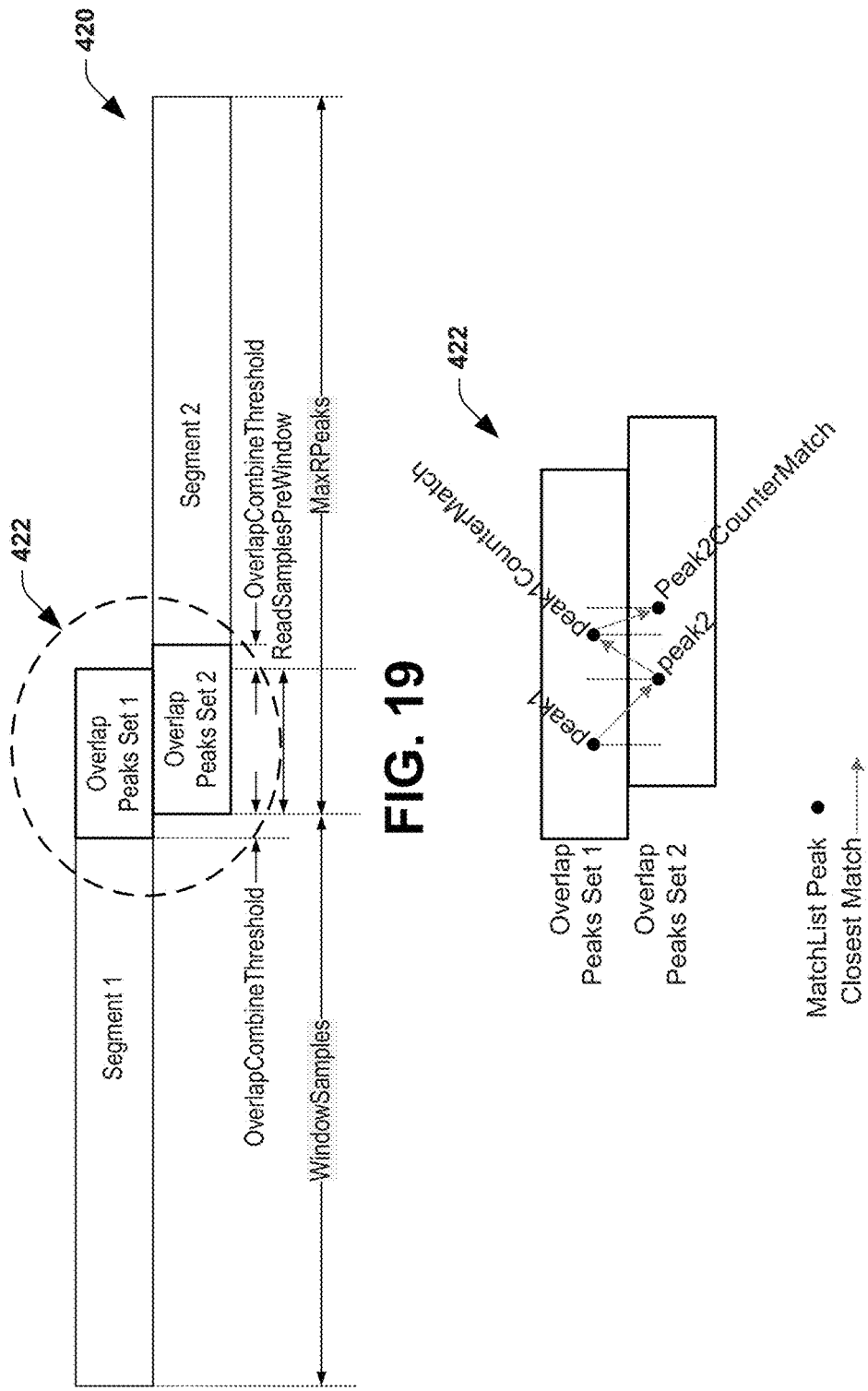

DETECTION AND ANALYSIS OF CARDIAC WAVEFORMS

CROSS-REFERENCE TO RELATED APPLICATION

This application claims the benefit of U.S. provisional patent application No. 62/331,103 filed on May 3, 2016, and entitled DETECTION AND ANALYSIS OF CARDIAC WAVEFORMS, which is incorporated herein by reference in its entirety.

TECHNICAL FIELD

This disclosure relates to detection and analysis of cardiac waveforms.

BACKGROUND

An electrocardiogram (ECG) system monitors electrical activity of a heart of a patient. A normal electrocardiogram includes a P wave, a QRS complex, and a T wave. During arrhythmogenic activity, such as fibrillation, tachycardia or bradycardia, the shapes of the different constituent parts of the waveform may distort from the normal sinus shapes. Such changes in waveform morphology can further complicate detection and analysis based on such waveforms.

SUMMARY

This disclosure relates to detection and analysis of cardiac waveforms.

As one example, a method includes performing amplitude-based detection to determine location of R-peaks for a plurality of electrograms. The method also includes performing wavelet-based detection to determine location of R-peaks for the plurality of electrograms. The method also includes adjusting the location of the R-peaks determined by the wavelet-based detection of R-peaks based on the location of R-peaks determined by the amplitude-based detection of R-peaks. The method also includes storing, in memory, R-peak location data to specify R-peak locations for the plurality of electrograms based on the adjusting.

As another example, a system includes a processor and non-transitory memory to store electrical data representing a plurality of electrograms and machine-readable instructions. The processor accesses the non-transitory memory and executes the machine-readable instructions. The instructions include amplitude peak detection code programmed to perform amplitude-based detection to determine location of R-peaks for a plurality of electrograms. Wavelet peak detection code is programmed to perform wavelet-based detection to determine location of R-peaks for the plurality of electrograms. Location adjustment code is programmed to adjust the location of the R-peaks determined by the wavelet-based detection of R-peaks based on the location of R-peaks determined by the amplitude-based detection of R-peaks. Code is also programmed to store in the memory R-peak location data to specify R-peak locations for the plurality of electrograms based on the adjusting. A display visualizes a graphical representation based on the R-peak location data.

As yet another example, a method may include performing principal component analysis on a selected region of interest with respect to a plurality of electrograms to define a QRST template. The method also includes correlating the QRST template relative to an interval of each of the plurality of electrograms to identify matching regions of interest. The method also includes removing the identified matching regions of interest from each of the plurality of electrograms using interpolation.

BRIEF DESCRIPTION OF THE DRAWINGS

FIG. 19 depicts an example of overlap regions between adjacent signal segments.

FIG. 20 is an enlarged example of the overlapped regions relative location matching logic.

DETAILED DESCRIPTION

Figure 1:
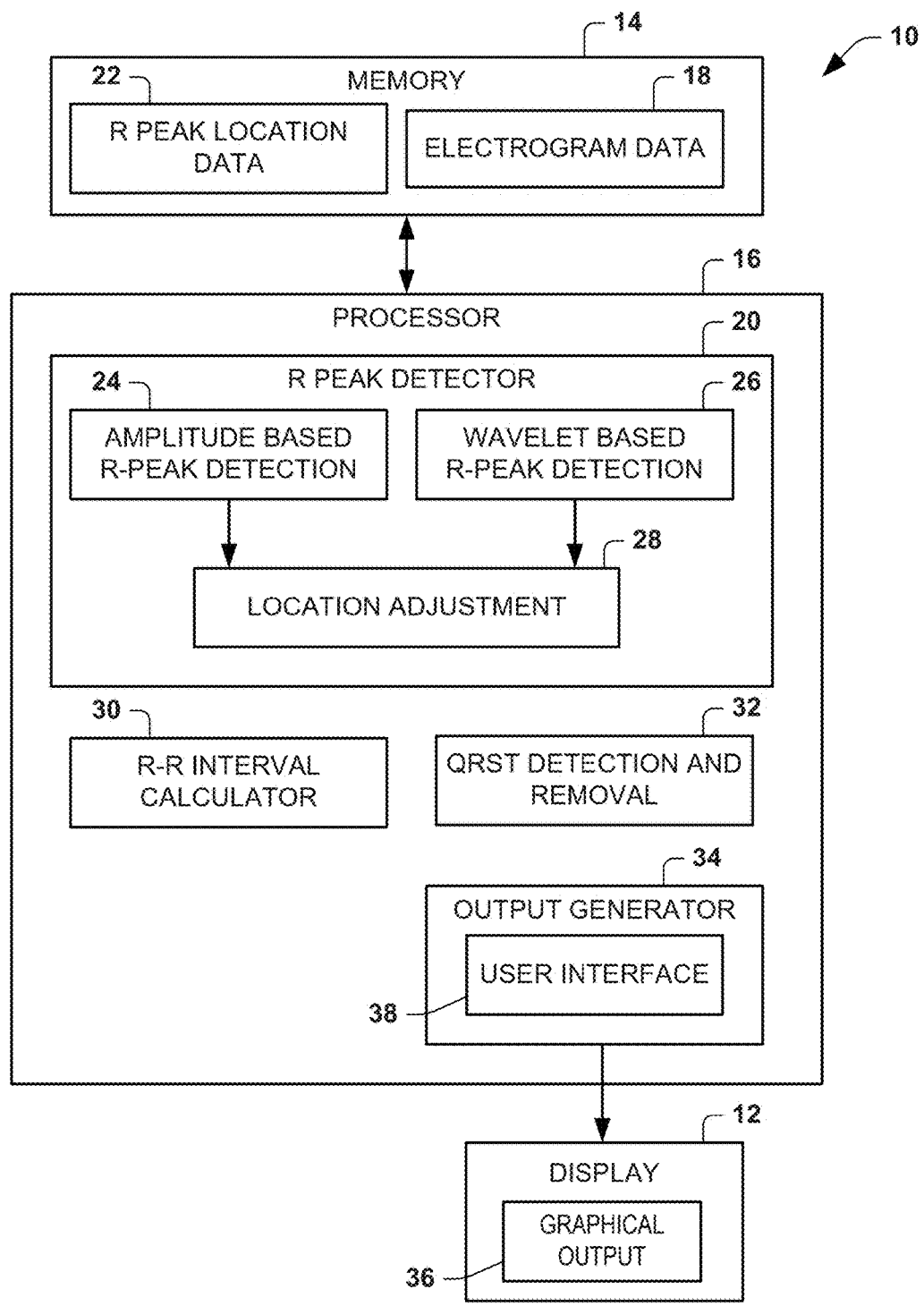
FIG. 1 depicts an example system to detect and analyze cardiac waveforms.

This disclosure relates to detection and analysis of cardiac waveforms, including detecting R-peaks and associated R-R intervals. The detection and analysis can also include detection and removal of QRST complexes from cardiac waveforms. The detected waveforms and associated analysis further can be used to drive an output to display corresponding to an interactive graphical map (e.g., a graphical user interface (GUI)).

As one example, systems and methods are disclosed to detect R-peaks of cardiac waveforms, namely electrograms (e.g., unipolar or bipolar) for one or more input channels. As one part, a baseline removal (e.g., filter) can be applied and peak amplitude detection used to identify R-peak locations in the waveforms (amplitude-detected R-peaks). Additionally, a wavelet-based R-peak detection can be employed to identify R-peak locations (wavelet-detected R-peaks). The amplitude-detected R-peaks and wavelet-detected R-peaks can be aggregated in a location adjustment phase in which the determined R-peak location is adjusted consistently with respect to the QRS complex morphology of each respective channel. The resulting R-peak locations can be stored in memory, such as identifying R-peak time indices for the cardiac waveforms in each respective input channel.

As another example, analysis of cardiac waveforms can be implemented by detecting and removing QRST complexes of cardiac waveforms. In this example, QRS and T are derived as a single template based on principal component analysis and the QRST template is applied to a selected region of interest (e.g., selected manually, semi-automatically or automatically). In some examples, the R-peak detection disclosed herein can be utilized to identify the beginning of the QRST complex of each waveform. In response to removing the QRST portion from the waveform, corresponding to ventricular activity, users can effectively and efficiently evaluate atrial activity in the remaining portion of the waveform, namely via P wave windows in respective electrograms.

As used herein, an electrogram refers to a graph of voltage over time that can be recorded one or more channels based on an electrical signal sensed by each electrode. For example, the electrograms for the heart can be generated from intracardiac or body surface measurements, which can include bipolar or unipolar electrograms. In some examples, the electrograms are reconstructed electrograms on a cardiac envelope that are computed by solving an inverse problem based on electrical signals acquired from a set of non-invasive body surface measurements and geometry data that relates the body surface measurement locations with respect to the cardiac envelope. In this case both the measured electrical signals on the body surface and the reconstructed electrical signals can be electrograms.

In some examples, the R-peaks can be utilized to drive a beat detection method, such as by suggesting one or more beats to users automatically according to the R-R intervals meeting prescribed criteria (time threshold). For instance, systems and methods herein can identify (highlight) each R-R interval that is determined greater than a specified duration, which may be a default or user-configurable length value. A user can accept the suggestions for further evaluation and mapping of such intervals, in response to a user input, or discard the suggested beat in response to another user input. For instance, an output generator is programmed to selectively filter and display cardiac waveforms based on established parameters (e.g., user defined and/or default values), such as to include beats having a duration (corresponding to R-R intervals) that exceeds a minimum threshold time interval or that are less than a threshold. The filter parameters thus can be set to select which beats to include in (or exclude from) an output map, which can vary depending on the type of maps being generated and the clinical interest of the user.

FIG. 1 depicts an example of a system 10 to detect and analyze cardiac waveforms as well as to generate graphical maps that can be visualized on a display 12. The system 10 includes memory 14, which can include one or more non-transitory machine-readable media. The system 10 also includes a processor 16, which can include one or more processing cores, to access the memory and execute corresponding instructions demonstrated within the processor block 16.

In the example of FIG. 1, the memory 14 stores electrogram data 18. The electrogram data 18 can correspond to unipolar electrograms, bipolar electrograms or other types of cardiac signals that can be measured or estimated. In some examples, the electrogram data 18 corresponds to raw electrogram signals that are measured non-invasively via sensors placed on an outer surface of the patient's body (e.g., an arrangement of body surface sensors distributed non-invasively across an outer surface of a patient's body, such as the patient's thorax or a portion thereof). As another example, the electrogram data 18 can include raw electrogram signals that are measured invasively via sensors placed within the patient's body (e.g., a catheter having contact or non-contact electrodes). In yet another example, the electrogram data 18 includes reconstructed electrograms onto a cardiac envelope of the patient's heart (e.g., an epicardial or other internal anatomic or virtual surface) by solving the inverse problem with respect to electrical signals. Various measurement systems (not shown in FIG. 1, but see measurement system 566) can be utilized to acquire the body surface electrical measurements that can be utilized to provide the electrophysiological data 18 that can either correspond to live data that is acquired intraprocedurally, or the electrophysiological data 18 can correspond to data that has been acquired a priori, such as part of a previous electrophysiology (EP) study or acquired during another intervention. The measurement system may measure the cardiac electrical activity via contact or non-contact sensors.

The processor 16 executes machine readable instructions that include an R-peak detector 20 to detect R-peaks in electrogram data 18. As an example, the R-peak detector 20 processes raw (e.g., non-line filtered) electrogram data 18 for one or more selected time intervals of each of the plurality of input channels. The R peak detector 20 employs amplitude- and wavelet-based methods to determine R-peak locations. The determined R-peak locations can be stored in memory as R-peak data 22 specifying time stamps (indices) or other tags for R-peak locations determined for electrograms in each channel.

As a further example, the R-peak detector 20 includes amplitude-based R-peak detection code 24. The R-peak detection code 24 employs a baseline removal process to remove the gradual drift of the signals, such as due to natural phenomenon (e.g., respiration, variations in electrode impedance, etc.). As one example, the baseline removal is Butterworth filter with a low pass cutoff frequency (e.g., $5^{th}$ order Butterworth filter with cutoff frequency of about 2 Hz). The baseline removal is selectively applied channels meeting certain signal criteria. For example, the amplitude-based R-peak detection code 24 employs the baseline removal to those channels which are not saturated (contain a constant value outside of +/−512 mV) or to channels determined not to be of low signal integrity (applied only to good channels). For instance, the signal integrity is determined by an acquisition assisted bad channel detection method that is executed on the data window to be processed (see, e.g., FIG. 3).

The amplitude-based R-peak detection code 24 also includes executable instructions to detect the R-peaks based on amplitude detection. Amplitude can be used to detect the R-peaks within EGG signals; however, there are situations where amplitude detection may become unstable. Due to this instability, amplitude-based R-peak detection is used by R-peak detector 20 as a check to confirm valid R-peaks determined via the wavelet-based R-peak detection disclosed herein. The local peaks are determined on a per channel basis from the maximum envelope using the refractory period as the minimum distance between the peaks. As used herein, the local peaks correspond to peaks that occur relatively close to each other in time (e.g., within some predetermined time period). For instance, when the binning occurs to determine the relative location of the R-peak, there may be multiple peaks that are detected in the complete histogram analysis but local peaks occur in a relatively small location. Also as used herein, the refractory period refers to the minimum time in which two R-peaks can occur, which may be a default or configurable value. The maximum density locations are determined as the R-peak locations with respect to all channels. The maximum density locations may include the amplitude and/or wavelet detected peak detections. In some situations, channels determined to be "bad channels" may be removed (e.g., manually or automatically) to leave a remaining set of "good channels," and in such circumstances, maximum density locations are determined as the R-peak locations with respect to such remaining set of channels (see, e.g., FIG. 4).

The R-peak detector 20 also includes wavelet-based R-peak detection code 26. For example, the wavelet-based R-peak detection code 26 implements a multi-tree complex wavelet transform that employs two real discrete wavelet transforms. The wavelet-based R-peak detection code 26 is programmed to compute coefficients (e.g., both detailed and approximate) from input signals by recursively using a high-pass and a low-pass filtering in combination with down sampling operations (see, e.g., FIG. 10).

By way of example, the wavelet-based R-peak detection code 26 can implement a dual-tree complex wavelet transform to decompose the input signal up to 6 levels (default, parameter is configurable). The last level of decomposed signal is used to find R-peak locations (relative R-peak locations) in plurality of samples (e.g., user configurable parameter—default can be at least 150 samples) apart from each other (refractory period). The wavelet-based R-peak detection code 26 further employs a moving average filter of a predetermined length (e.g., user configurable parameter default can be 200 samples) to distinguish noise from the peaks (detection filter length) (see, e.g., FIG. 5).

The wavelet-based R-peak detection code 26 further determines the R-peak location (a refinement of the R-peak locations determined above). The wavelet-based R-peak detection code 26 provides the detected locations of the R-peaks for each channel. For example, the wavelet-based R-peak detection code 26 determines the R-peak locations with respect to all of the channels based on a histogram that is generated for the detected locations, peak detection based on a refractory period, padding of the detections, peak detection based on a minimum count height, and a final check for missed peak detection (see, e.g., FIGS. 6 and 7).

The R-peak detector 20 also includes a location adjustment function 28 to combine the R-peaks determined by detection functions 24 and 26. For example, the adjustment function 28 adjusts each wavelet detected R-peak to place the detection at a consistent location relative to the QRS complex morphology for each respective channel. For instance, when viewing a single channel, the R-peak can be determined at a single time instance. When viewing multiple channels, however, the R-peak will not occur at the same exact time sample when comparing channels. Therefore, as used herein, the relative location is the time location in which R-peak is most prominent and most representative of the R-peak in all channels. Since the R-peak is relative with respect to all channels (e.g., only good channels, as mentioned) and morphology of the QRS complex varies from channel, the location chosen for the R-peak location by wavelet-based detection 26 may not be consistently chosen for similar QRS morphologies. Thus, the adjustment function 28 compares the wavelet detected R-peak locations to the amplitude detected R-peak locations for accuracy of the detection. For example, in response to identifying wavelet detections that do not have corresponding amplitude detections, the location adjustment function 28 further verifies such detections based on evaluation of the refractory period between peaks and the detected peaks at neighboring nodes.

The location adjustment function 28 of the R-peak detector returns final R-peak locations for the evaluated ECG data and such locations are stored in memory as the R-peak data 22. In some examples, to efficiently process acquired ECG Data, the R-peak detector 20 can implement a windowing method to ensure accurate detections and reduce processing time, such as disclosed herein (see, e.g., FIGS. 19-21).

As disclosed herein, the processor 16 also executes instructions corresponding to an R-R interval calculator 30 to compute the RR-interval lengths based on the R-peak location data 22. For instance, the R-R interval calculator 30 computes R-R intervals as the difference between time stamps for each adjacent pair of R-peaks in each respective channel. The RR interval thus is utilized to identify respective heart beats for further processing and evaluation. For example, if the RR-interval is greater than a specified length (can be defined in response to user input), the interval may be displayed in a list (e.g., in display 12) for the user to review and/or apply additional signal processing and analysis methods.

In the example of FIG. 1, the processor 16 also executes instructions corresponding to QRST detection and removal function 32. The QRST detection and removal function 32 processes the signals across channels to remove ventricular signal components to facilitate analysis of atrial signals. The QRST detection and removal function 32 generates a QRST template that combines QRS complex and T wave into a single template region of interest.

For example, the QRST detection and removal function 32 performs PCA on a selected region of interest, such as can be selected automatically or manually in response to a user input identifying an interval of signal corresponding to QRST complex. The PCA can thus be used to generate a QRST template definition that can be applied across the time frames, such as by time stepping the template with respect to ECG data to be searched to determine correlation coefficients. The peak correlation coefficients are used to identify potential locations in which the virtual template matches the template. The correlation coefficients can be compared to a threshold to identify corresponding regions of interest for each of the channels.

The QRST detection and removal function 32 can remove each region of interest and perform spline interpolation to automatically connect adjacent P waves. As an example, the interpolation can be implemented as a shape-preserving piecewise cubic interpolation (e.g., Piecewise Cubic Hermite Interpolating Polynomial (PCHIP) or another spline interpolation function). Such an interpolation function keeps the interpolated values monotonic (e.g., either increasing or decreasing) based on the ending point values used for such interpolation. The processor 16 can implement baseline removal and/or remove bad input channels prior to executing the QRST detection and removal function 32, such as disclosed herein.

An output generator 34 can be utilized to generate one or more graphical outputs 36 that can be presented on the display 12. For example, the output generator 34 can display a plurality of electrograms, such as can be acquired for a plurality of measurement locations distributed across a body surface (invasively or non-invasively) or derived from measurements of electrical activity over a surface of the patient's body (e.g., an external and/or internal surface), such as disclosed herein. The output can also include a list of calculated R-R intervals associated with one or more (e.g., up to including all) channels, which can be a complete list or a selected subset thereof according to which intervals meet selection criteria (e.g., one or more user defined or default thresholds).

The output generator 34 can also include a user interface 38 that can be utilized to set parameters for controlling which electrograms are included in the output 36 in response to user input, and to otherwise interact with and select portions of the electrophysiological data 18, such as disclosed herein. For example, the user interface 38 can specify minimum and/or maximum time interval parameters to apply to detected R-R intervals, and include in the interactive output only those meeting the specified parameters (and excluding the other intervals). For instance, in response to selecting a given one or more intervals from the list, the output generator 34 can generate a set of calipers that are placed at the start and stop times of the selected interval. The selected set of the intervals can be for a selected set of signals distributed across the surface or for the entire surface and for one or more time intervals of interest, which can be selected in response to a user input.

The output generator 34 can also generate one or more graphical maps 38 that can be presented on the display 12. For example, the output generator 34 can generate an activation map or other map representing arrhythmogenic activity, such as based on the channels following QRST removal. This can be for a selected set of the signals distributed across the surface or for the entire surface and for one or more time intervals of interest, which can be selected in response to a user input. Examples of the types of output visualizations and maps that can be generated are disclosed herein (see, e.g., FIGS. 29 and 30) as well as those disclosed in U.S. Pat. Pub. 2014/0336520, International Publication No. WO2014/113672 and/or International Publication No. WO2014/113672.

As disclosed herein, in some examples, the electrogram data 18 is spatially and temporally consistent across the entire surface on which the electrograms were measured or derived. As a result, the electrograms can be generated for the entire cardiac surface over one or more time intervals. The output generator 34 can employ the user interface to set parameters for the graphical map and to otherwise interact with and select portions of the electrophysiological data 18 in response to user input, such as disclosed herein.

R-Peak Detection

Figure 2:
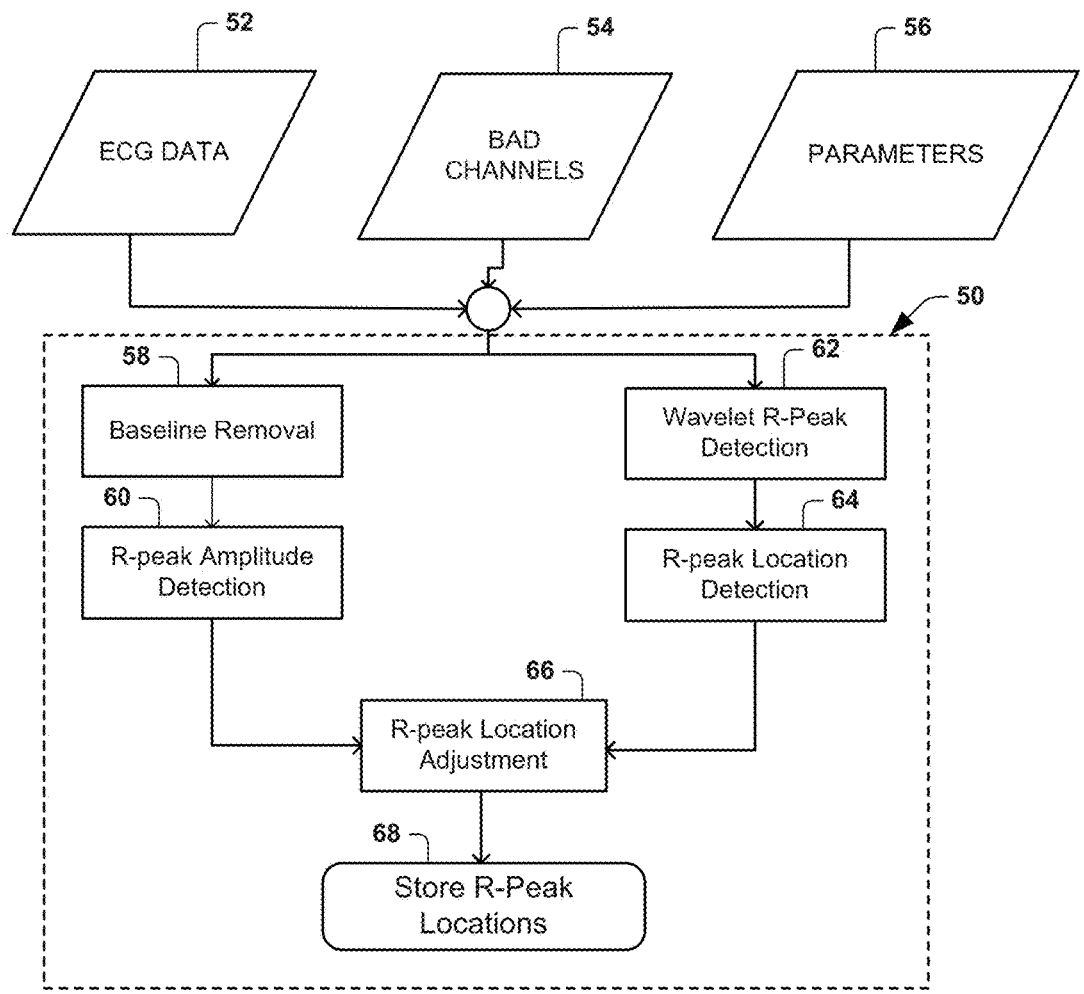
FIG. 2 depicts an example of a system to detect R-peaks in cardiac waveforms.

FIG. 2 depicts an example overview of an R-peak detection method 50, such as corresponding to R-peak detector 20 of FIG. 1. The R-peak detection method includes two paths from which the results are used for the final R-Peak determination (e.g., providing R-peak data 22). In FIG. 2, the inputs to the R-peak detection method include the ECG data segments for a time interval, a list of bad channels, and the input parameters. The left internal workflow entails removing the baseline from the ECG signal at 58 and then processing the ECG data for R-peak detections using only the amplitude as the discriminating factor (e.g., collectively corresponding to the amplitude-based R-peak function 24 of FIG. 1). The right internal workflow entails a wavelet peak detection method 62 and an R-Peak localization method 64 based on the wavelet peak detection results (e.g., collectively corresponding to the wavelet-based detection function 26 of FIG. 1). An R-peak location adjustment method 66 combines the amplitude- and wavelet-detected R-peaks for a final determination and adjustments to the R-peak detections (e.g., corresponding generally to the location adjustment function 28 of FIG. 1). The R-peak location adjustment method 66 outputs the sample locations relative to the input ECG data segment R-peak detections, such as stored in memory (e.g., R-peak data 22).

Figure 7:
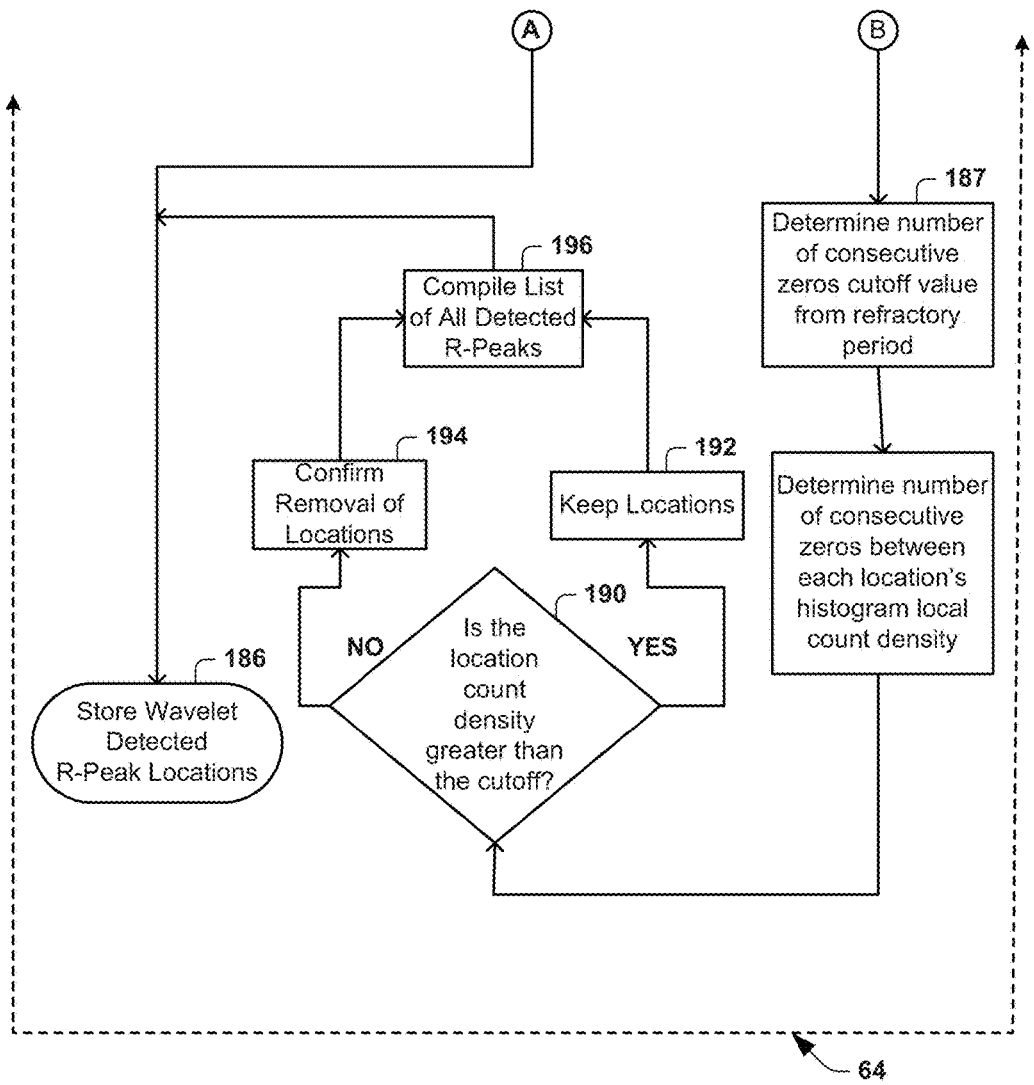
Figure 8:
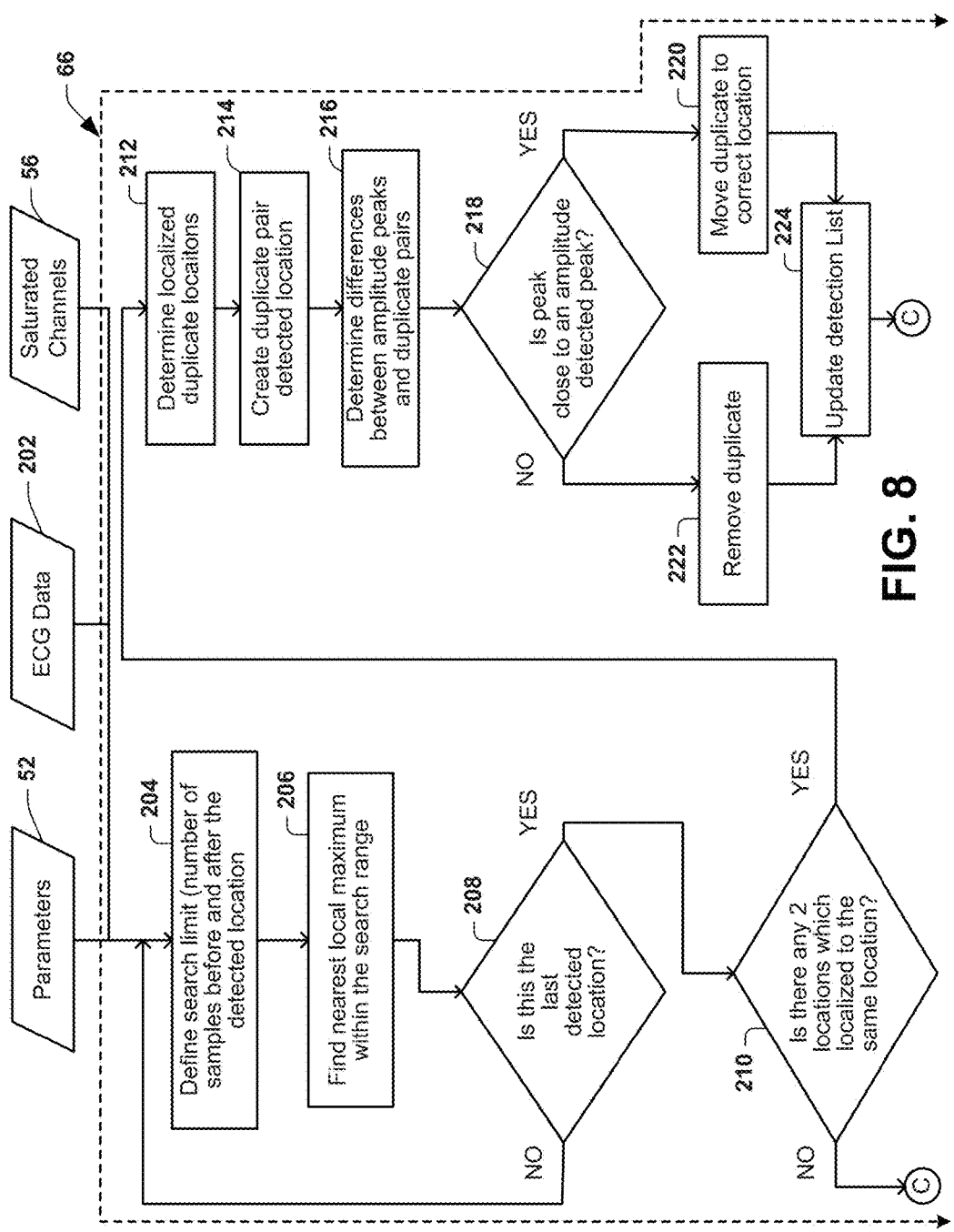
Figure 9:
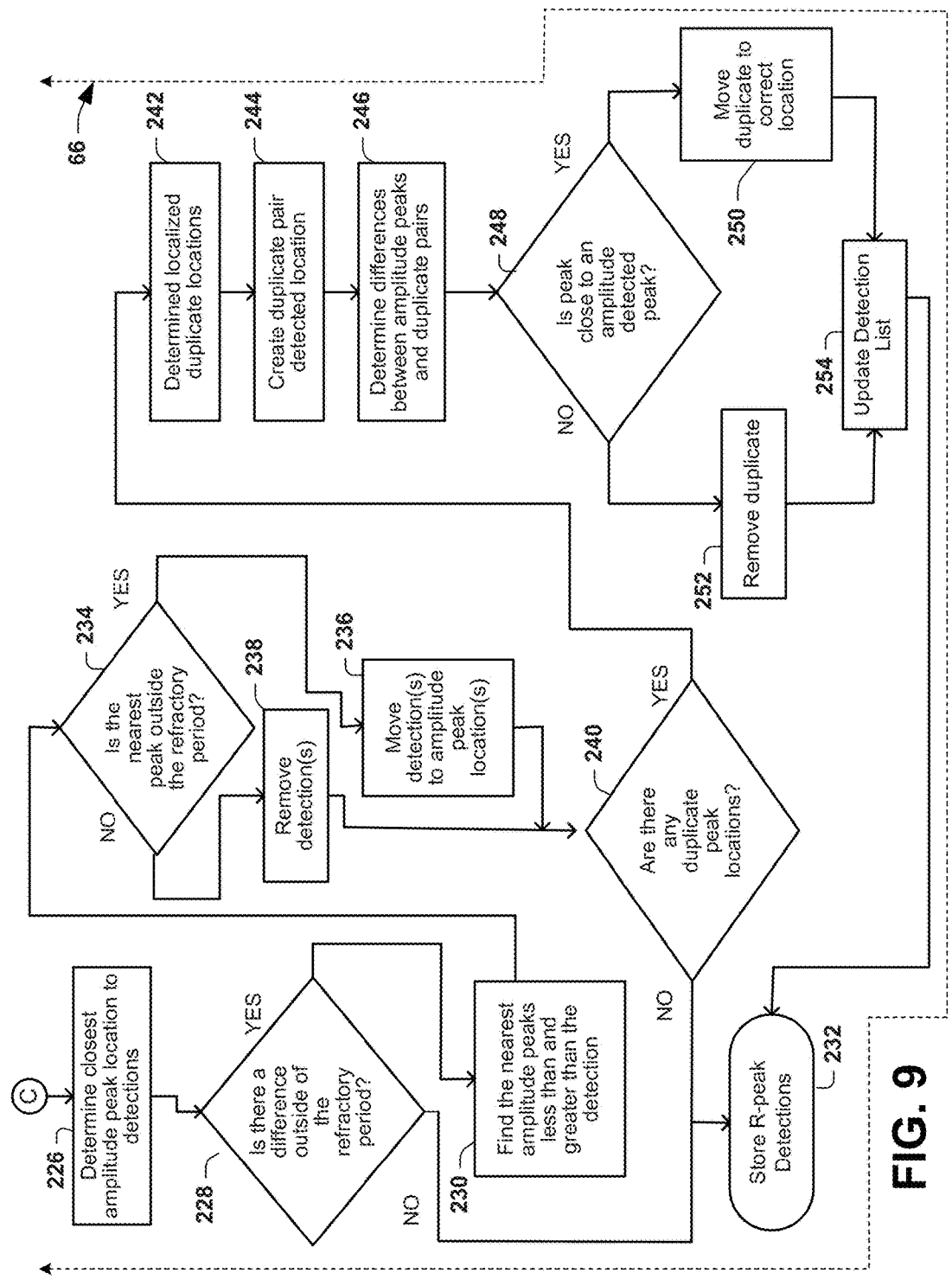

In the example of FIG. 2, the R-peak detection 50 method includes five functions, examples of which are demonstrated in this disclosure as follows: baseline removal (FIG. 3), R-Peak amplitude detection (FIG. 4), wavelet method for peak detection (FIG. 5), R-Peak location detection of the wavelet method detections (FIGS. 6 and 7), and R-Peak location adjustment (FIGS. 8 and 9).

Each function 58-66 can be a separate instruction code module that can be called and executed by the processor as needed. In some examples, only good channels for the interval are used for R-peak detection analysis. The bad channels (e.g., including bad, saturated/disconnected) are detected on the analyzed interval.

Baseline Drift Removal (58)

Figure 3:
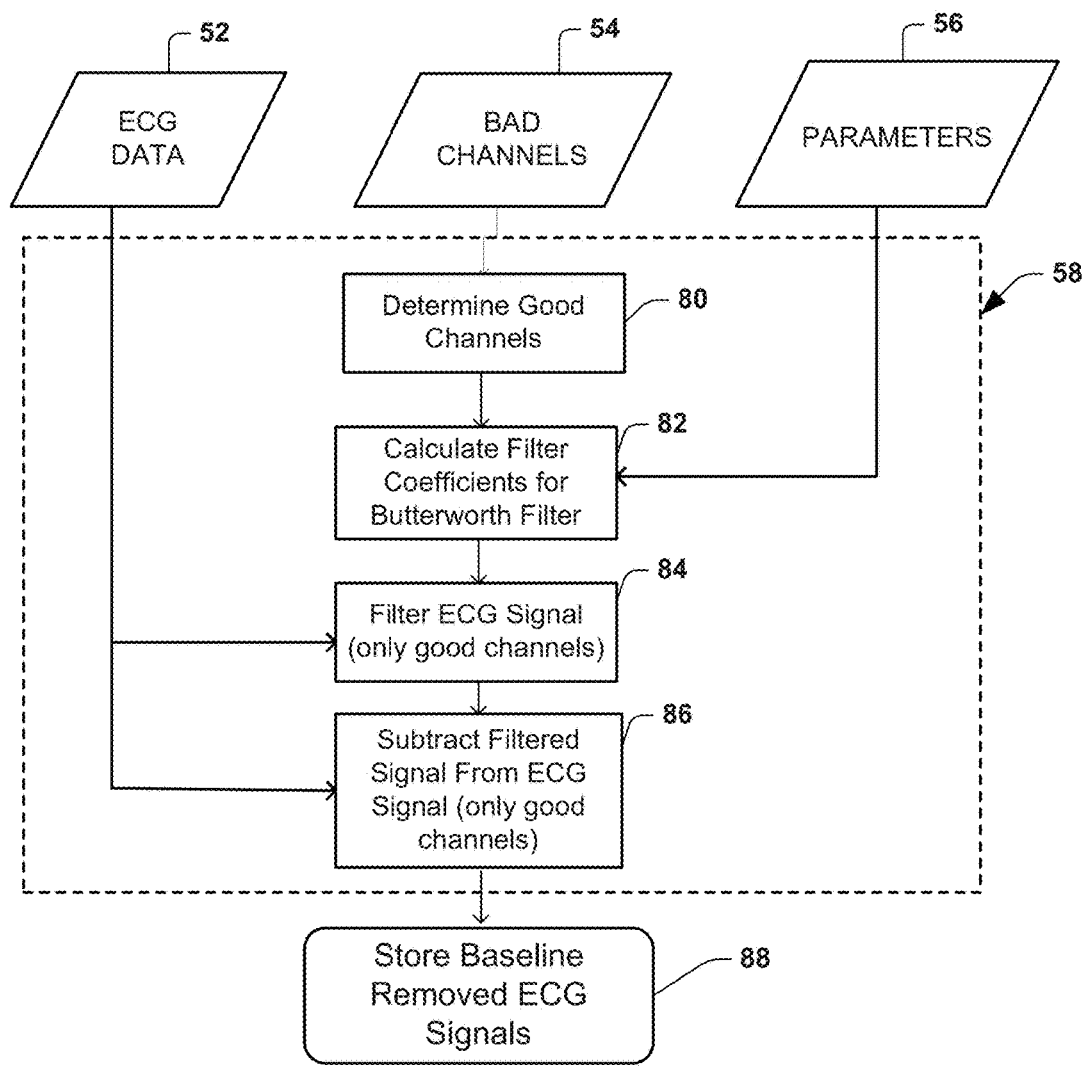
FIGS. 3-9 depict examples of various component parts of the R-peak detection system of FIG. 2.

As one example, FIG. 3 depicts an example of a baseline removal method 58, which utilizes the ECG data 52, bad channel information 54 and parameter data 56. At 80, the method determines a set of good channels for further processing. The good channels can define those channels that have not been tagged as bad channels (in data 54) or otherwise have been determined to have sufficient channel integrity (e.g., signal-to-noise ratio).

At 82, filter coefficients are determined. For example, the filter may be an $N^{th}$ order (e.g., N>3, such as $5^{th}$ order) Butterworth filter with a low pass cutoff of about 2 Hz. The filter is applied at 84 to the good channels of the ECG data, which define the channels which are not considered bad or saturated out of the complete set of input channels. At 86, this signal is the baseline signal and it is then subtracted from the input ECG data (only good channels) to create an ECG signal with no baseline trend. At 88, the baseline removed ECG signals are stored in memory for further processing by the R-peak amplitude detection method 60.

R-Peak Detection Using Only Amplitude

As mentioned, amplitude can be used to detect the R-peaks within ECG signals (e.g., by amplitude-based detection function 24 of FIG. 1); however, there are situations where amplitude detection can become unstable. As disclosed herein, detection via amplitude is used (e.g., by adjustment function 28 of FIG. 1) as a check to confirm valid R-peaks determined via wavelet-based R-peak detection (e.g., detection 26 of FIG. 1).

Figure 4:
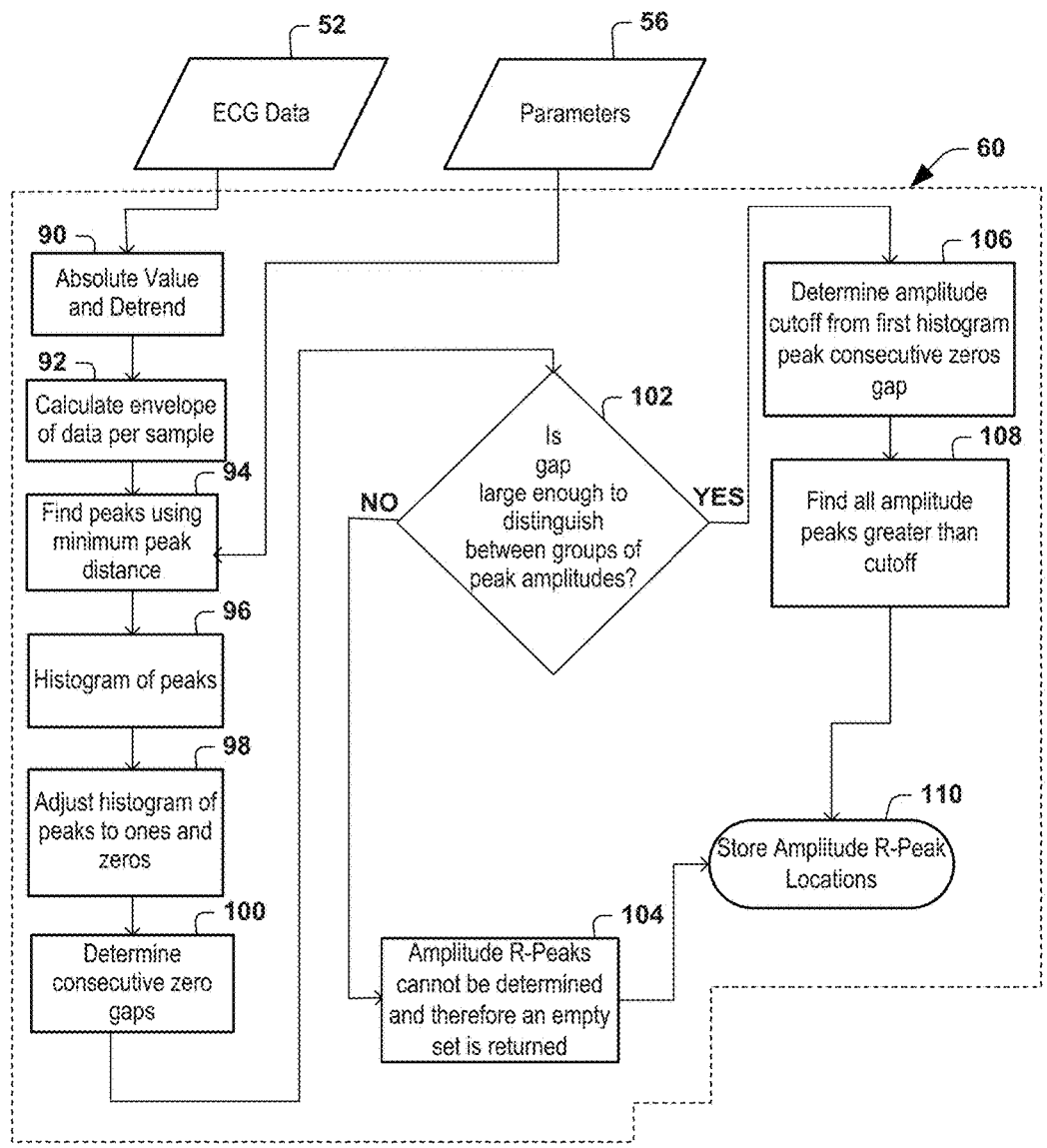
Figure 15:
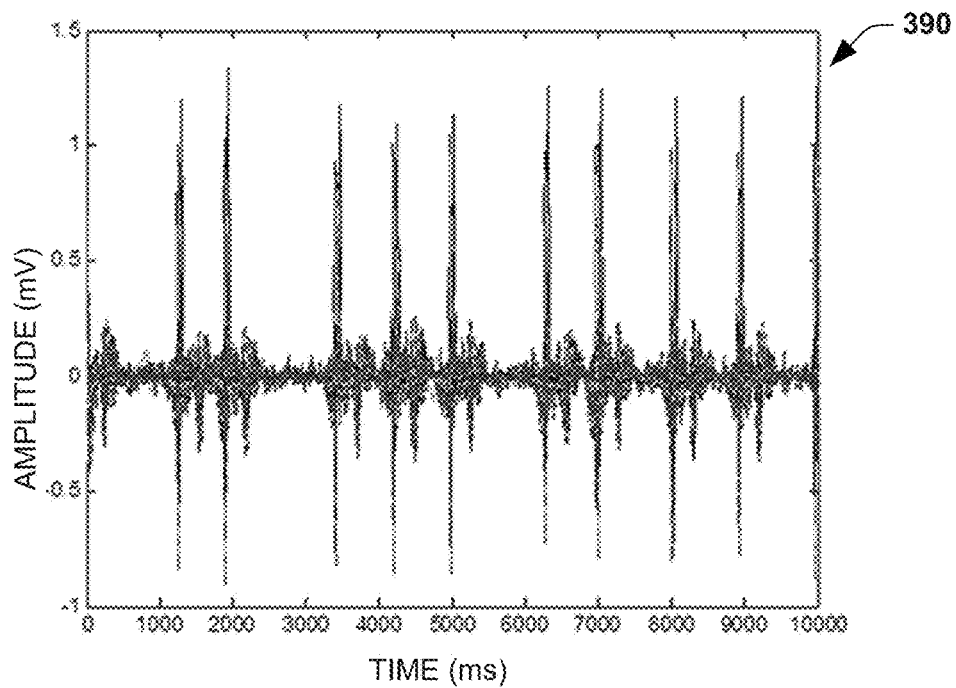
FIG. 15 depicts an example composite plot of an interval of an input signal.
Figure 16:
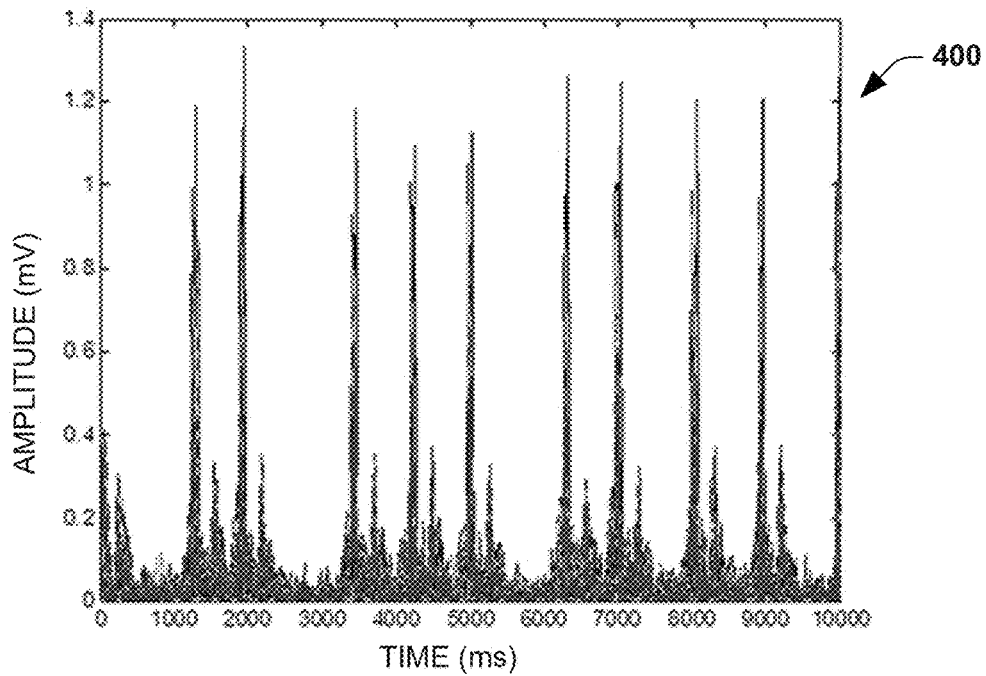
FIG. 16 depicts a composite plot of the absolute value of the input signal of FIG. 15.

FIG. 4 depicts an example of R-peak amplitude detection method 60. The R-peak amplitude detection method 60 employs ECG data 52 and parameter data 56. At 90, an absolute value of the ECG input signal is made. An example ECG input signal 390 is shown in FIG. 15. An absolute value of the example input signal of FIG. 15 is shown at 400 in FIG. 16. At 90, detrending is also performed, such as by filtering filtered to remove frequencies below about 2 Hz. At 92, the envelope of data per sample is calculated. At 94, peaks are located using minimum peak distance criteria. For example, the local peaks are determined from the maximum envelope using the refractory period as the minimum distance between the peaks. Inherently, there will be peaks detected of much lower amplitude than the R-peaks, as shown in FIG. 15.

Figure 17:
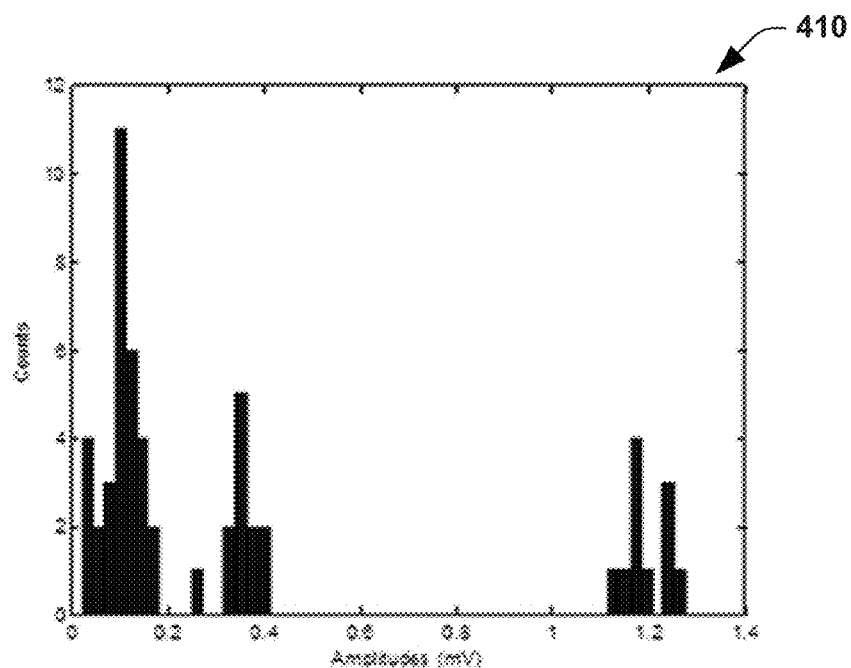
FIG. 17 depicts an example histogram of peak amplitude values.

At 96, peak values (amplitude values per peak, from 94) are histogrammed into bins (shown at 410 in FIG. 17). It can be seen from FIG. 17 that one or more groups of amplitudes can be determined by the density of points. At 98, the histogram of peaks is adjusted to ones and zeros. At 100, consecutive zero gaps are determined. For example, in FIG. 17, the first gap around 0.2 mV is 3, the second gap is 2, the third gap is 31 and the fourth gap is 1. All bins with no counts before the first count density and after the last count density can be ignored. The first gap, which is larger than the consecutive number of bins cutoff value (e.g., default=5), is set as the gap between the low amplitude and high amplitude channels.

At 102, a determination is made as to whether a gap is large enough to distinguish between two more groups of peak amplitude. If the determination at 102 is negative (NO), the method proceeds to 104. At 104, where amplitude R-peaks cannot be determined, an empty set is returned based on the determination. If the determination at 102 is affirmative (YES), the method proceeds to 106.

Figure 18:
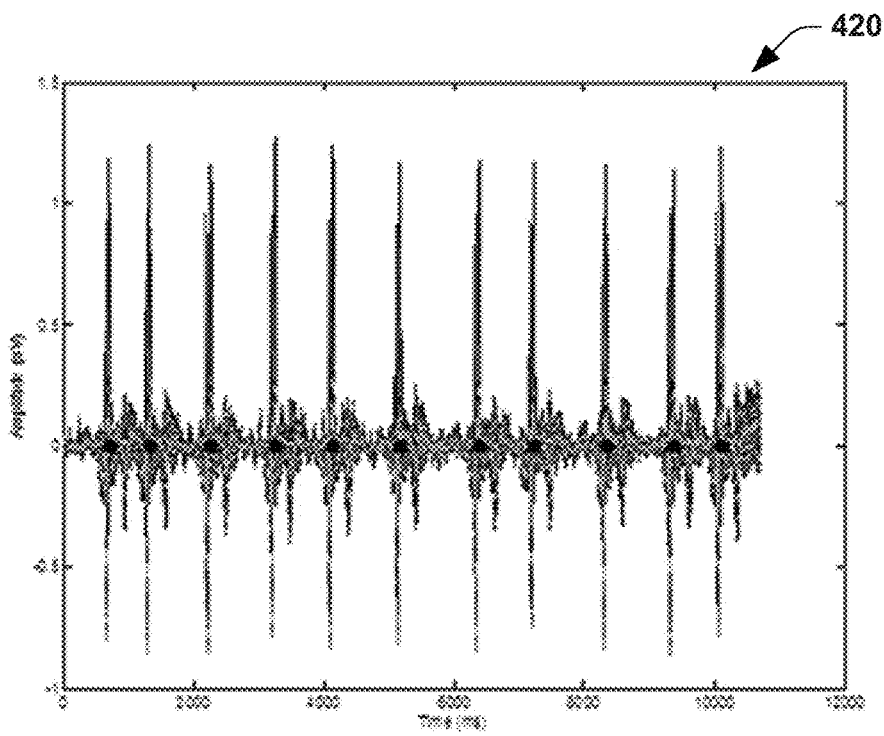
FIG. 18 depicts an example of a plot of an input signal with R-peak detections detected by amplitude.

To detect only the higher amplitude peaks, it is necessary to determine a cutoff value to discriminate amplitudes. The cutoff value may be determined from the amplitude at the middle of this gap. For example, in FIG. 17, the cutoff bin is determined as bin 34 which represents an amplitude of about 0.7857 mV. All peak detections greater than this cutoff value are kept as amplitude R-peak detections. At 106 an amplitude cutoff from the first histogram peak is determined as the consecutive zero gap. At 108 all amplitudes having the peaks greater than the cutoff are determined. An example of the R-peak detections via amplitude detection is shown at 420 in FIG. 18 via markers along the X-axis. At 110, the amplitude R-peaks are stored in memory (e.g., memory of 22).

Peak Detection Using the Wavelet Method

Figure 5:
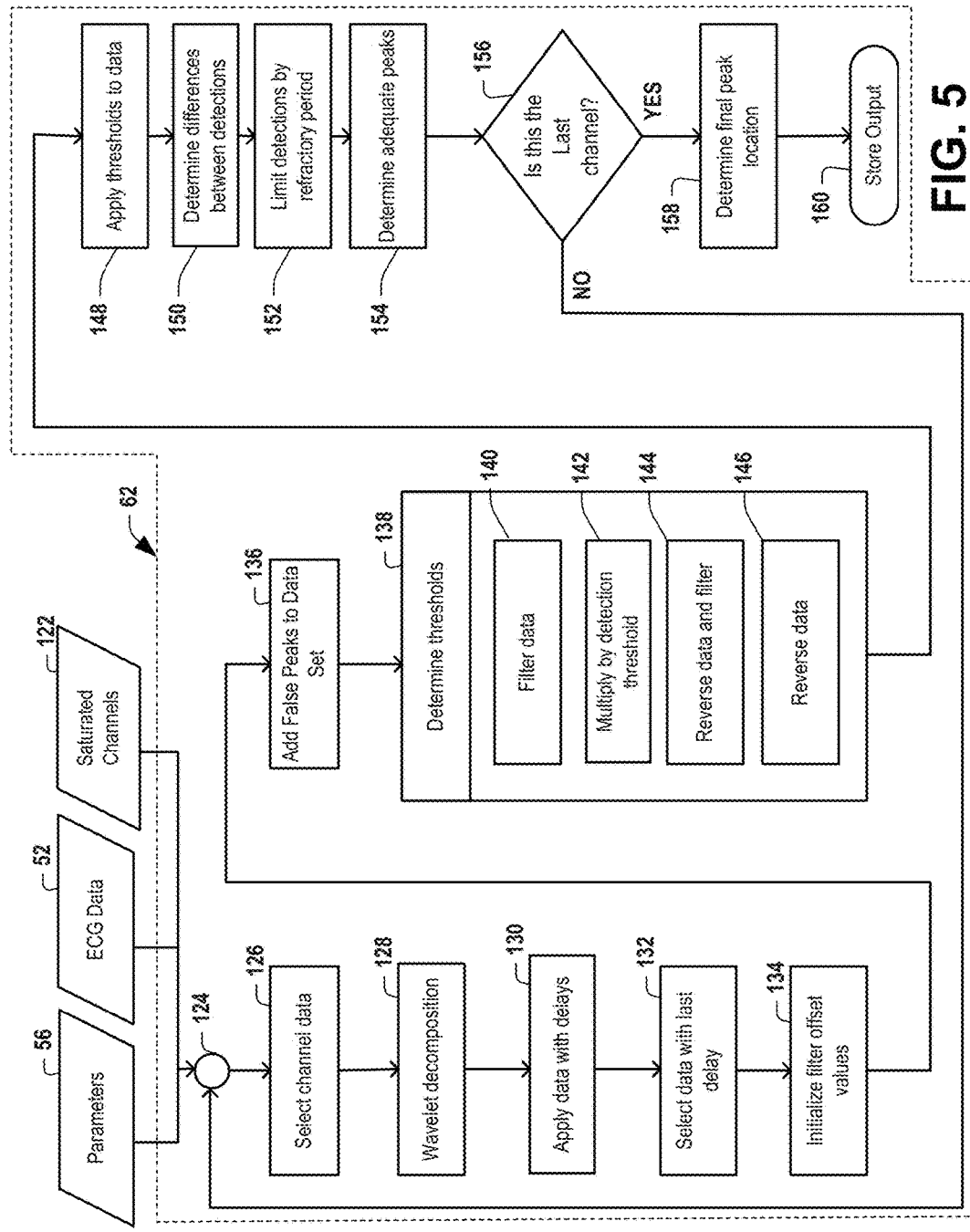

FIG. 5 depicts an example of the wavelet R-peak detection method 62, which is used to determine the estimated peak locations. The detection method 62 utilizes the ECG data 52, parameters 56 and information about saturated channels demonstrated at 122. Saturated channel data can be utilized by applying a saturation threshold to each of the channels to determine whether the channel is saturated or contains information that resides within saturation limits. The input data is combined, indicated at 124, for processing for each respective channel. At 126, channel data is selected for wavelet R-peak detection. At 128, wavelet decomposition is implemented. At 130, data is applied with delays and, at 132, data without delays are selected. At 134, a filter offset values are initialized (e.g., 20).

At 136, false peaks are added to the end of the data set for further processing. At 138 thresholds are determined. Such determination can involve use of filter data 140. The filter data can be multiplied by detection threshold at 142 and the data can be reversed and filtered to provide corresponding reverse data at 146. Corresponding thresholds are applied at 148 to the corresponding data. At 150, differences are determined between the respective detections according to the applied thresholds. At 152 detections are limited by the refractory period such as disclosed herein. At 154, adequate peaks are determined within the refractory period. At 156, a determination is made as to whether the current processing of the method 62 was for the last channel. If it is not the last channel, the method returns to 124 to detect the next channel data. If it is the last channel, the method proceeds from 156 to 158 to determine the final peak location. From 158 the method proceeds to 160 and the output data is stored in memory for the wavelet-based R-peak locations.

By way of example, the wavelet R-peak detection method 62 implements a dual-tree complex wavelet transform (DTCWT) employs a plurality of real DWTs (discrete wavelet transforms); the first DWT provides the real part of the transform while the second DWT provides the imaginary part. The method computes the coefficients (detailed and approximate) from input signal by recursively using a high-pass and a low-pass filter in combination with down sampling operations.

Figure 10:
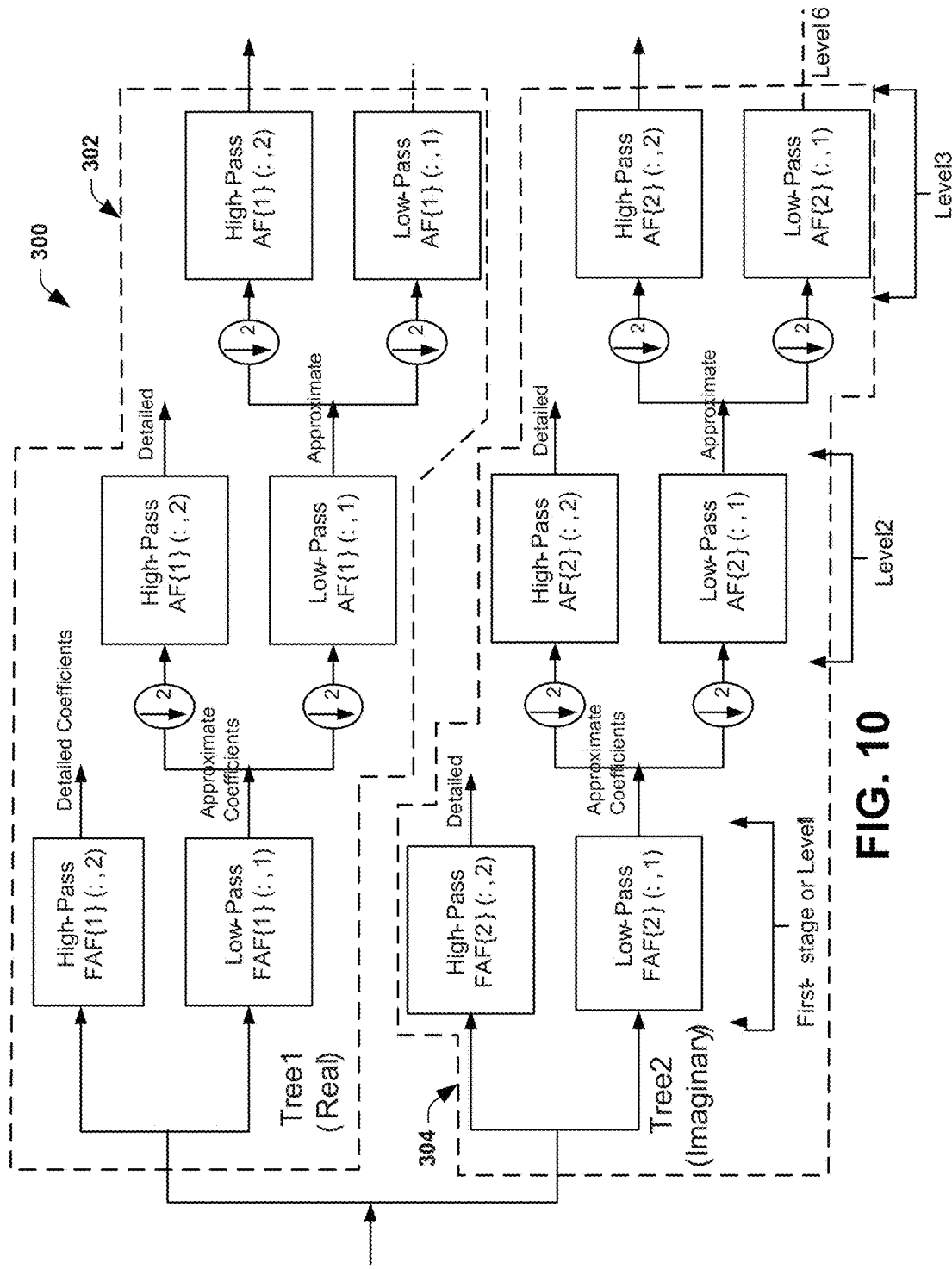
FIG. 10 depicts examples of a complex wavelet transform that can be utilized in the R-peak detection method.

FIG. 10 shows an example of a DTCWT 300 that includes two trees 302 and 304, such as can be utilized by wavelet R-peak detection method 62. As mentioned, the outputs from tree 1 are the real coefficients while the outputs from tree 2 are imaginary. The real and imaginary parts are simply added to give the final complex coefficients of the $i^{th}$ level decomposition.

Each tree has a high and a low pass filter at each level. The high-pass filter coefficients are obtained from low pass filter coefficients, such as follows:

$$g(k)=(-1)^k h(N-k) \qquad \text{Equation 1}$$

where $g(k)$ are the high-pass filter coefficients of level k, N are the wavelet coefficients, and $h(N-k)$ are the low-pass filter coefficients.

In order to satisfy the reconstruction conditions and to be approximately analytic, the two real wavelets from each of the two real wavelet transforms are Hilbert transforms of each other.

Application of Multi-Tree Complex Wavelet Transform

Figure 11:
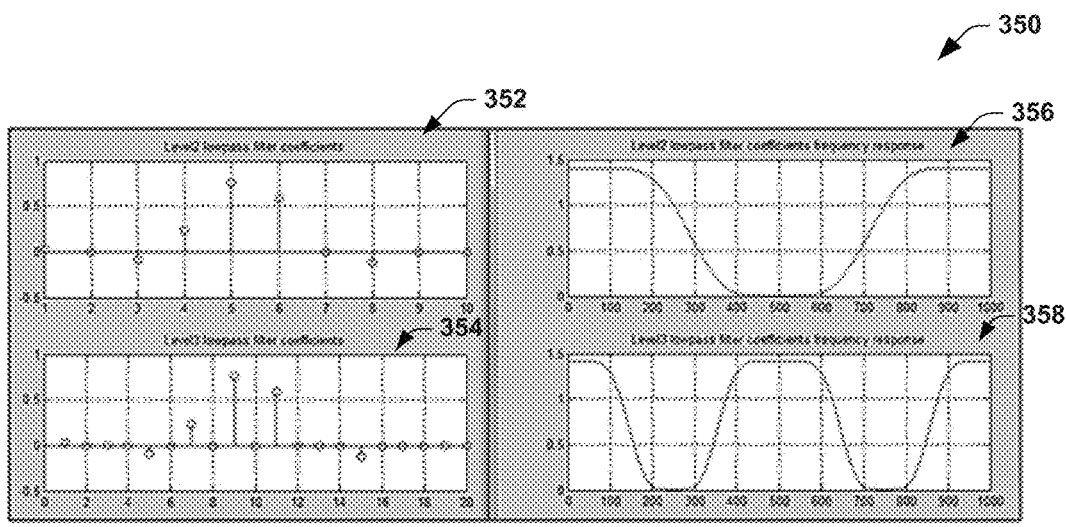
FIGS. 11 and 12 depict examples of filter coefficients for a tree of the complex wavelet transform of FIG. 10.
Figure 12:
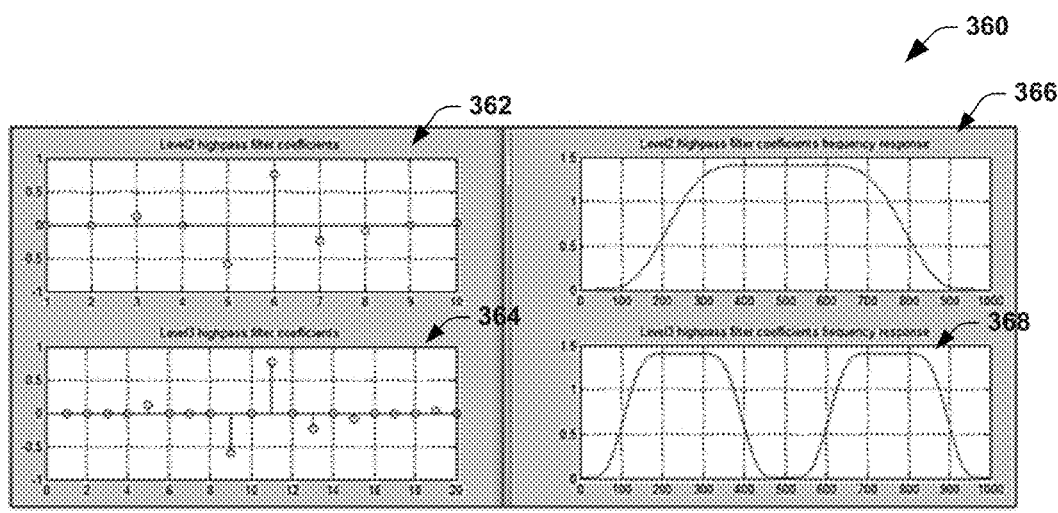

By way of further example, the R-peak detection function (e.g., R-peak detector 20 of FIG. 1) uses the DTCWT to decompose the input signal up to 6 levels. The filters coefficients of second tree are obtained from first tree by vertically flipping the first tree coefficients. The down sampling of the input signal is obtained by zero-padding filter coefficients at even samples. This has an effect of halving the frequency bands. FIGS. 11 and 12 show examples of plots 350 and 360 that demonstrate the second and third level low pass filter coefficients 352 and 354 second and third level high pass filter coefficients 362 and 364 for first tree. Plots also show the corresponding low pass frequency responses at 356 and 358 and high pass responses 366 and 368, and the effect of zero-padding (e.g., using Matlab's function dyadup or similar function) for low-pass and high-pass filters.

The low-pass filtered coefficients are further decomposed through high-pass and low-pass filters until the desired level is reached. Each level of decomposition reduces the frequency resolution by a factor of 2. The last level of decomposed signal is used to find R-peaks locations spaced a predetermined number of samples (e.g., at least 150 samples) apart from each other (e.g., corresponding to the refractory period). A moving average filter of a prescribed length (e.g., about 200 samples) can be used to distinguish noise from the peaks (e.g., a configurable detection filter length).

Filtering introduces a delay which causes lag of the filtered data after filtering at each level. This lag is accounted for correct localization of the peaks with respect to the input signal. For instance, the delay time (e.g., shown in Row 4 of TABLE 1) is added to the respective level of the filtered data for correct locations of R-peaks.

Delay Calculations

TABLE 1

| Row | | Levels of Decomposition | | | | | |
|---|---|---|---|---|---|---|---|
| | | 1 | 2 | 3 | 4 | 5 | 6 |
| 1 | Filter Orders | 110 | 20 | 40 | 80 | 160 | 320 |
| 2 | FIR Filter Delays (Cascaded) | 55 | 15 | 35 | 75 | 155 | 315 |
| 3 | Compensation | 00 | 2 | 4 | 8 | 16 | 32 |
| 4 | Implemented Delays in samples (Row2-Row3) | 55 | 13 | 31 | 67 | 139 | 283 |

The output of the function is the relative sample location of the wavelet detections per channel relative to the input data.

Determine R-Peak Locations Based on Wavelet Detections

Figure 6:
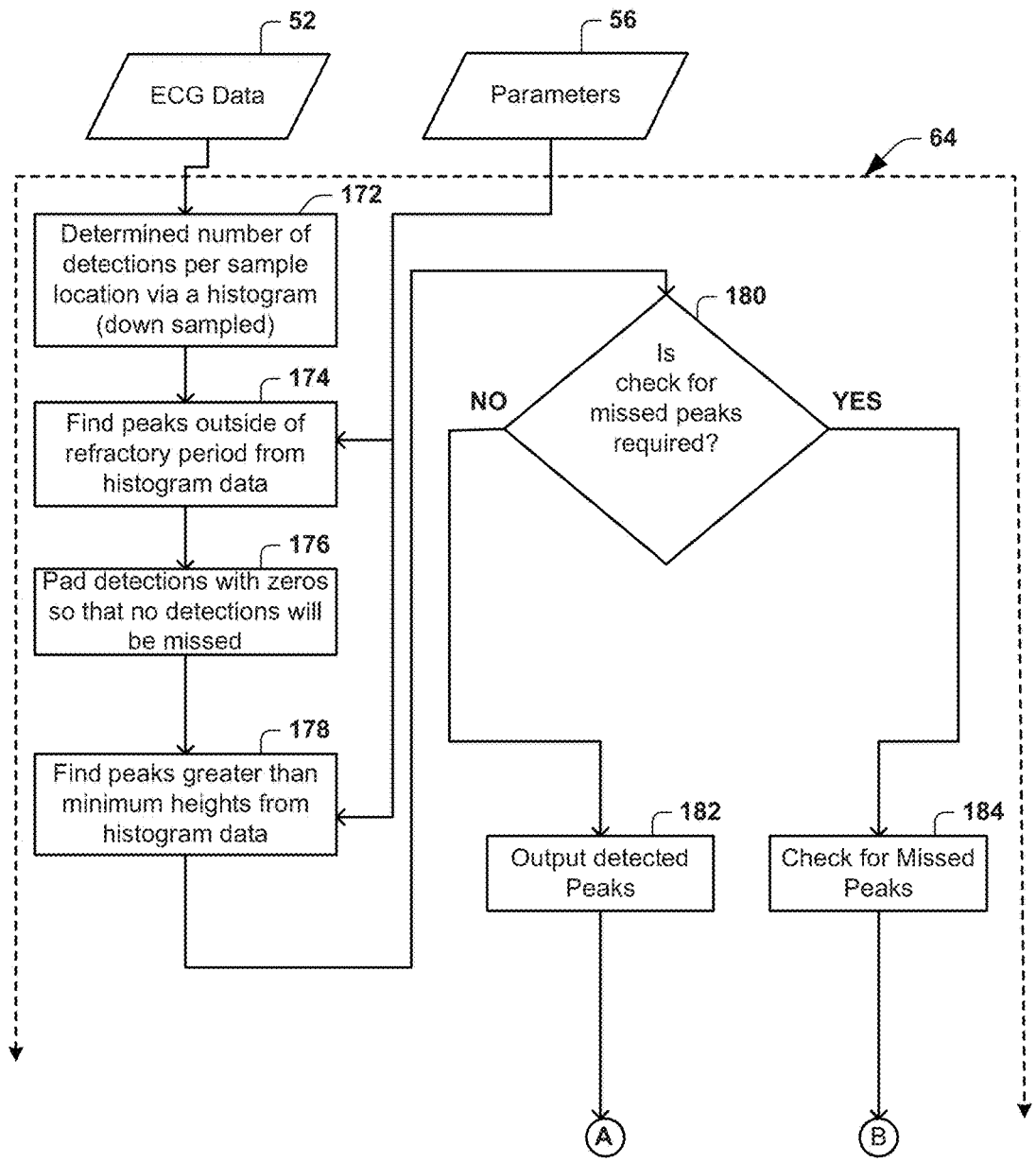

FIGS. 6 and 7 depict an example of R-peak location detections method 64 (corresponding to detection function 26 of FIG. 1). The R-peak location detections method 64 employs ECG data and parameter data 56. The wavelet R-peak detection method 64 provides the detected locations of the R-peaks per channel. In many channels, not all of the R-peaks are detected whereas in other channels all or different R-peaks are detected. To more accurately determine the relative location of the R-peaks with respect to all channels, the wavelet peak detections need to be processed further. The process to determine the R-peak locations with respect to all of the channels may include a histogram of the detected locations, peak detection based on a refractory period, padding of the detections, peak detection based on a minimum count height, and a final check for missed peak detections.

At 172, the number of detections per sample location is determined via a histogram which can involve down sampling. The histogram method is used to refine the detected R-peak locations. The binned data is then used to determine local peaks based on a minimum peak separation as defined by the refractory period. For example, the refractory period is defined as the minimum time in which two R-peaks can occur. As one example, a default value for the refractory period is approximately 150 ms. This value is derived from the knowledge that the minimum time between two ventricular activations would be approximately 150 ms. At 174, peaks outside of the refractory period are determined from the histogram data, and peak detections within the refractory period (too close in time) are eliminated. The local peak count and local peak location are calculated and padded with zeros. This is done to mitigate missing detections from the undetermined detections. For instance, the zero padding adds zeros in between each peak count in order to improve the second peak detection which used a minimum height, or in this case count, requirement to mitigate false detections. After the false detections are removed, the detected locations can either be stored in memory or be further evaluated for missed detections.

At 178 peaks that are greater than a minimum height from the histogram data are located. At 180, a determination is made as to whether a method is required to check for missed peaks. This determination can be based on a number of peaks in the relevant data set. If it is not necessary to check the peaks, the method proceeds to 182 to output the detected peaks. If it is necessary to check for missed peaks, the method proceeds to 184 to check for missed peaks. For example, detections could be missed in scenarios where the wavelet detection method detected an R-peak at many locations within a small region which would result in a low count for the binning process and would be removed during the second peak detection. The check for missed peaks relies on the density of detections nearest a possible detection location. For each peak detection from the first peak detection, the onset and offset of the concentration of counts around the detection is calculated. From this, the total number of counts within the density region is determined.

FIG. 6 is connected with FIG. 7 via connectors A and B. Thus from 182, via connector A, the method proceeds to 186 in which the output detected peaks can be stored as wavelet detected R-peak locations in memory. From 184, the method can proceed to 187 to determine the number of consecutive zeros cutoff value from the refractory period. At 188, the number of consecutive zeros between each location's histogram local count density is determined.

From 188, a determination is made at 190 whether the location count density is greater than the cutoff threshold. For example, by evaluating the number of counts per density region and comparing those counts to a threshold, which may be calculated from 10% of the maximum density region count, it is possible to reconcile a previously removed detection and add it back to the detection list. Once all density regions are evaluated, the list of detections to be added back, if any, are added to the wavelet peak detection list. If the determination at 190 is affirmative, the method proceeds to 192 and the locations are kept. If the location count density is determined to be not greater than the cutoff, however, the method proceeds from 190 to 194 to confirm the removal of the identified locations. From each of 192 and 194 the method proceeds to 196 to compile a list of all detected R-peaks.

Figure 13:
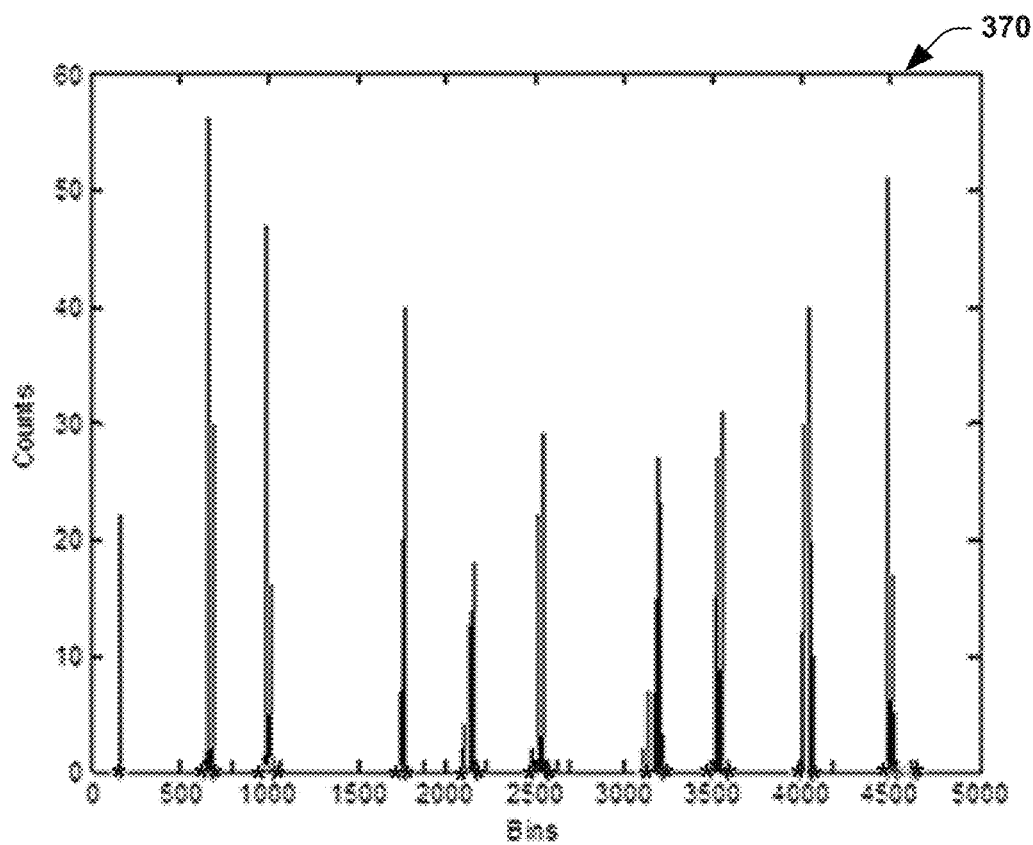
FIG. 13 depicts an example histogram plot of wavelet detected peak locations.
Figure 14:
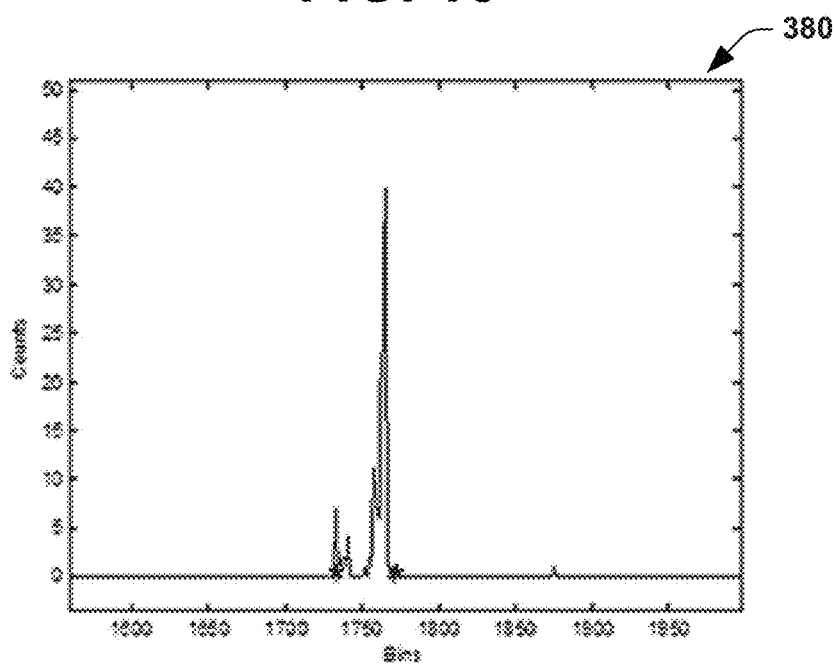
FIG. 14 depicts an enlarged view of part of the plot of FIG. 13 demonstrating detected peak locations for a range of bins 1550 and 2000.

From 196 the method proceeds to 186 to store the wavelet detection R-peak locations as mentioned above. For example, the wavelet peak detection locations per channel are combined into a single array. This array contains the location detections independent of the channels which will allow for an unbiased per channel evaluation of the R-peak locations. A bin counted histogram is calculated from this array, such as using half the number of data samples as the input ECG data. The histogram process results in the counts of the R-peak detections on a per sample basis, such as the histogram plot 370 shown in FIG. 13. A zoomed view of part of FIG. 13 is shown at 380 in FIG. 14.

R-Peak Location Adjustment

Each wavelet detected R-peak is adjusted to place the detection at a consistent location relative to the QRS complex morphology. Since the R-peak is relative to all channels (only good channels) and morphology of the QRS complex varies, the location chosen for the R-peak location may not be consistently chosen for similar QRS morphologies. An adjustment method (e.g., adjustment method 28 or 66) adjusts the R-peak relative to the QRS morphology.

FIGS. 8 and 9 demonstrate an example of the R-peak location adjustment method 66 (corresponding to method 28). The R-peak location adjustment method 66 utilizes ECG data 52, parameter data 56 and the detected R-peaks 202 provided at 110 and 186. At 204, a search limit is defined. For example, the search limit can be the number of samples before and after the detected location. The search limit is defined as the number of samples before and after the detected location to search for a local maximum (on per channel basis). A default search limit in number of sample can be set to a predetermined value (e.g., about 250 samples) or the search limit can be configurable. At 206, a nearest local maximum within the search limit can be found. The local maxima are calculated for each channel within the search region based on a shorter refractory period (e.g., about 100 samples) and a maximum location count (e.g., about 4 counts). The local maxima peaks can be determined by using the method of determining the peaks based on peak location counts mentioned above. The sample locations of the suggested local maxima are evaluated for the highest peak count. This location is assigned to the wavelet detected location. A list of all of the adjusted locations is compiled respective to the previously wavelet detected location.

At 208, a determination is made as to whether the current location is the last detected location in the data set. If determination is negative, the method can return to 204 to repeat the process. If it is the last detected location, the method proceeds from 208 to 210. At 210, a determination is made as to whether there are any two locations which are localized to the same location. If no two locations are localized in the same location, the method can proceed, via connector C, to 226 (FIG. 9). If two locations are localized at the same location, the method can proceed to 212 for performing a duplicate removal function demonstrated at 212 through 224.

As an example, at 212, localized duplicate locations are determined. At 214, a duplicate pair detected location is created. At 216, differences between the amplitude peaks and duplicate pairs are determined. At 218, a determination is made as to whether the peak is close to a corresponding amplitude detected peak. For example, a nearest amplitude detected R-peak to R-peak detection is determined based on a number of samples before and after the detected location, considered the search region defined by a search limit. If the determination at 228 is negative, meaning that the peak is not close to the amplitude detected peak, the duplicate is removed at 222. If the peak is determined to be close to the amplitude detected peak, the method proceeds to 220 and the duplicate is moved to a correct location such as to the adjacent next amplitude peak location. At 224, the detection list is updated. From 224 the method proceeds via connector C to 226.

At 226 the closest amplitude peak location is determined with respect to the detections. At 228, a determination is made as to whether there is a difference outside of the refractory period for the determination at 226. If there is no difference outside of the refractory period (it is within the refractory period), the method proceeds to 232 to store the corresponding R-peak detection location in memory. If there is a difference outside of the refractory period, the method proceeds from the 228 to 230. At 230, the nearest amplitude peaks that are less than and greater than the detection is located. At 234, a determination is made as to whether the nearest peak is outside the refractory period. If the next determination is positive, meaning that the nearest peak is outside of the refractory period, the method proceeds to 236 in which the detection is moved to the amplitude peak location. If the determination 234 is negative, the detections are removed. Thus, wavelet detections which do not have a corresponding amplitude detection are not used, and the method further analyzes the peaks to ensure that the detected peaks are separated by at least the amount of the refractory period. From each of 236 and 238, the method proceeds to 240.

In some examples, the reassignment of the detected location will reassign two wavelet detections to the same new location. In order to prevent this, the peak adjustment can utilize a duplicate detection method. At 240, a determination is made as to whether there are any duplicate R-peak locations. If there are no duplicate R-peak locations, the method proceeds from 240 to 232 to store the corresponding R-peaks detections. If there are duplicate peak locations, the method proceeds from 240 to perform a duplicate removal process that can be identical to the process at 212 through 224.

For example, peak detections are evaluated for duplicates. If no duplicates exist, the duplicate detection is skipped; otherwise the detection pair is identified. A detection pair is the two index locations within the adjusted detections vector which were assigned the same location. The duplicate detection also calculates differences between the amplitude detections and wavelet R-peak detections. This results in an array from which the wavelet detections can be localized to the amplitude detections. The array is used to determine if one of the duplicate pairs has been assigned to the incorrect location. Next, the nearest amplitude peaks are determined for each of the duplicate detection pairs. If the detections are not associated to the same amplitude peak, then the detection location farthest from the amplitude peak is reassigned to the farther amplitude peak location. If the detections are associated to the same peak, the first duplicate detection is removed. This process is repeated for all duplicate pairs.

Another part of the R-peak adjustment function 66 is to detect outlying detections. This is accomplished by comparing the amplitude peak detections with the adjusted peak detections. If the detection is within the refractory period of the adjusted peak detection, then it is removed from the detections. However, if the detection is outside of the refractory period, it is moved to the nearest amplitude peak location. By reassigning the location to the nearest amplitude peak, it is necessary to again check for duplicate locations as done in the preceding duplicate detection process. This same process can be repeated to double check for duplicate detections. Finally, the list of all adjusted R-peak detections is compiled to be returned.

Example Implementations for R-Peak Detection

Figure 21:
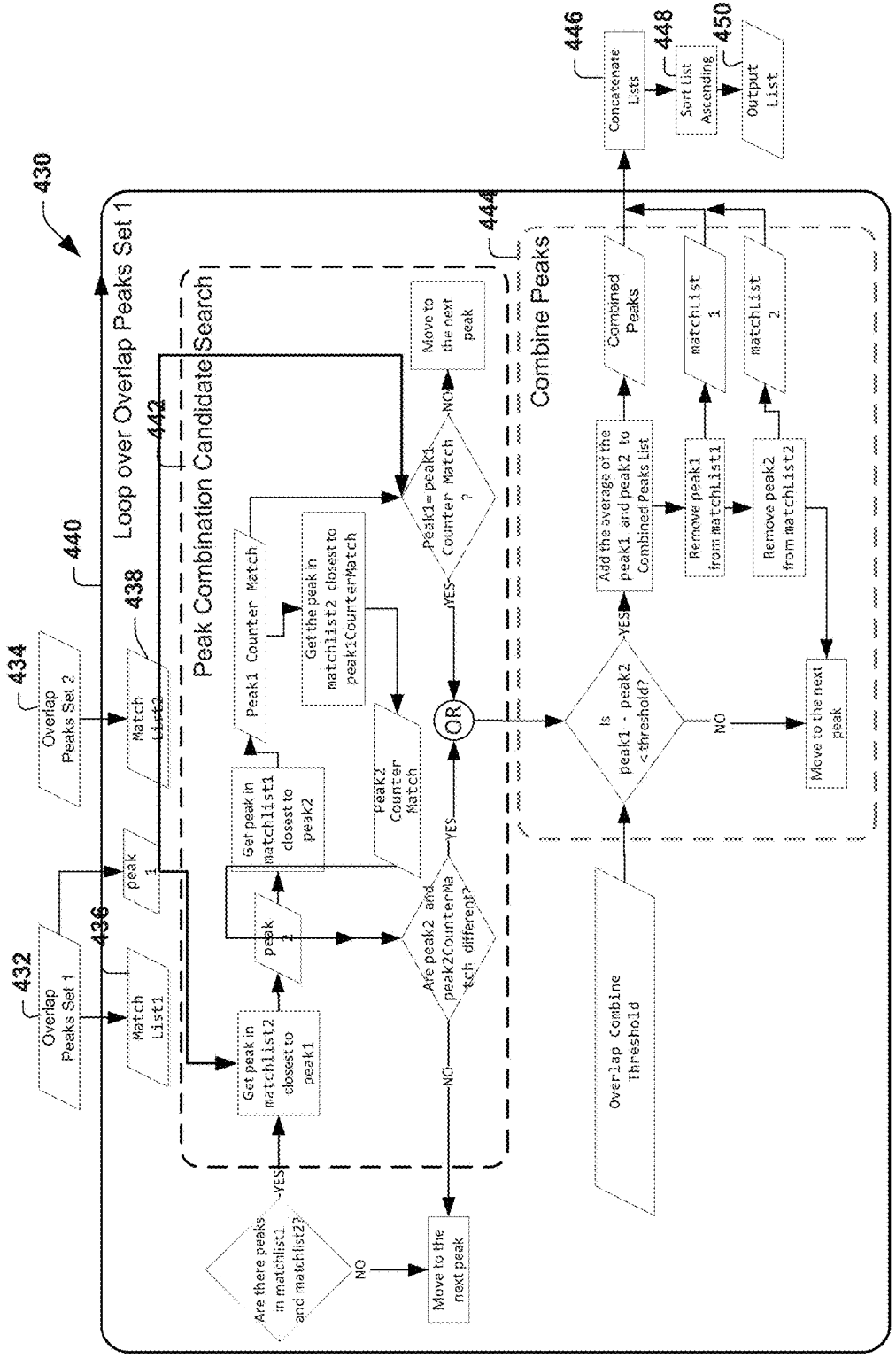
FIG. 21 depicts an example of a logic diagram that can be utilized to determine overlap between respective peaks.

By way of further example, the R-peak detection method is designed to analyze data in a windowing method. Referring to FIGS. 19-21, in some examples, to efficiently process acquired ECG Data, the R-peak detector 20 can implement a windowing method, demonstrated between adjacent time segments at 420. The windowing method helps to ensure accurate detections and reduce processing time. For example, the data are processed as a window of data having a predetermined time interval (e.g., default of about 10 seconds—can be configurable). The window is time shifted through the ECG data set with a small overlapped region (e.g., about 700 ms or another configurable time interval). The window overlap occurs at the end of the previous window with the beginning of the current window. For an example sampling rate of about 1000 samples/second, the total window size is 10700 samples. The window overlap occurs at the end of the previous window with the beginning of the current window. Therefore, the last 0.7 seconds of the previous window and the first 0.7 seconds of the current window are the same but processed in two different windows.

The overlap helps to ensure the detections at the beginning and the ends of the window are correct. Additionally, the first previous window overlap region start time is increased by a small window (e.g., a configured time interval or a default value, such as about 150 ms) in the past while the current window overlap region end time is increased by small window (e.g., a configured time interval or a default value, such as 150 ms) in the future. The elongation of the overlap regions accounts for detections at the edge of the window to ensure no edge detection(s) is (are) missed. The R-Peaks are returned per window and combined to provide the R-Peak location data (e.g., R-peak data 22), which R-peak location can be time indexed with respect to the complete electrogram data set (electrogram data 18).

When the windows overlap, it is possible to get detections which refer to the same exact R-peak, same relative R-Peak, and/or different R-Peaks. In some examples, the R-peak detected locations will be the same. In this case, the duplicate detection is removed and one detection remains. In another example, the detected location will be in the same relative location but not at the exact same location. The same relative location is defined as having a maximum location difference of less than or equal to a predetermined number of samples (e.g., about 150 samples or milliseconds). To correct this situation, the averaged location of the two locations is used as the detected R-peak location and the original two detections are removed. In the scenario where a new detection is determined for a window, the relative distance to the other detections is checked and if it is outside the range (about 150 ms), then the new detection is added to the detection list. FIG. 20 shows the overlapped region 422 relative location matching logic.

FIG. 21 shows an example of a window overlap logic diagram 430. The logic utilizes sets of overlapping peaks 432 and 434 to generate match lists 436 and 440 to identify peaks that match within respective overlapping regions (e.g., region 422). The logic provides a peak for segment 1, at 438, to combination candidate search 442 to locate matching peaks in the overlapping region between segments. The logic further implements a combine peaks method to adjust the match lists 436 and 440 to accommodate matching peaks. The combined peaks are utilized to concatenate respective lists at 446. The list can be sorted at 448 and the list can be output at 450.

QRST Detection and Removal

As disclosed herein, systems and methods disclosed herein can detect and remove QRST complexes. For example, instead of treating QRS and T as separated entities, the approach herein treats them as a single entity.

Figure 22:
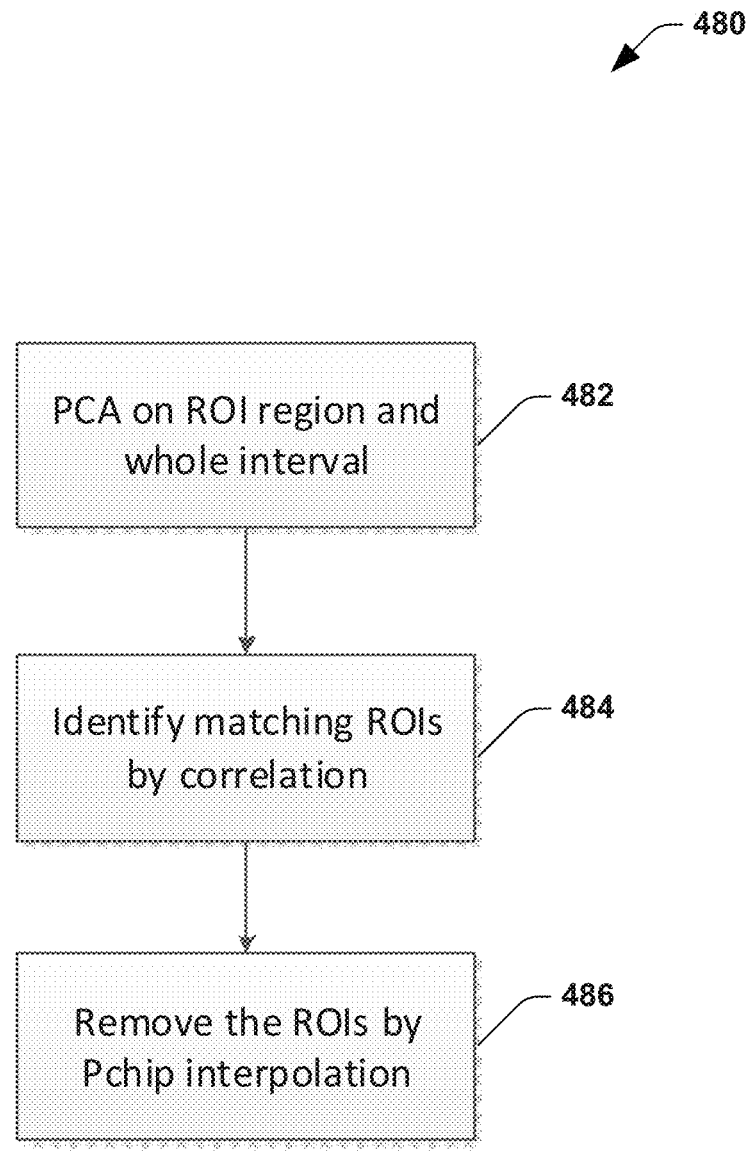
FIG. 22 is a flow diagram depicting an example method to remove QRST complexes from a cardiac waveform.

FIG. 22 is a flow diagram depicting an example method 480 to remove QRST complexes from a cardiac waveform, such as can be implemented by QRST detection and removal function 32 of FIG. 1. At 482, the QRST detection and removal function performs PCA on a selected region of interest. The region of interest may be selected automatically or manually in response to a user input identifying an interval of signal corresponding to QRST complex. The PCA can thus be used to generate a QRST template definition. At 484, the template can be applied across the time frames to identify matching regions of interest correlation, such as by time stepping the template with respect to determine correlation coefficients. The peak correlation coefficients are used to identify potential locations in which the virtual template matches the template. The correlation coefficients can be compared to a threshold to identify corresponding regions of interest for each of the channels.

At 486, each region of interest can be removed and interpolation (spline interpolation) performed to connect adjacent P waves, automatically. As an example, the interpolation can be implemented as a shape-preserving PCHIP function or another spline interpolation function. Such an interpolation function keeps the interpolated values monotonic (e.g., either increasing or decreasing) based on the ending point values used for such interpolation. Baseline removal may be performed and/or bad input channels removed prior to executing the QRST detection and removal method 480, such as disclosed herein.

Figure 23:
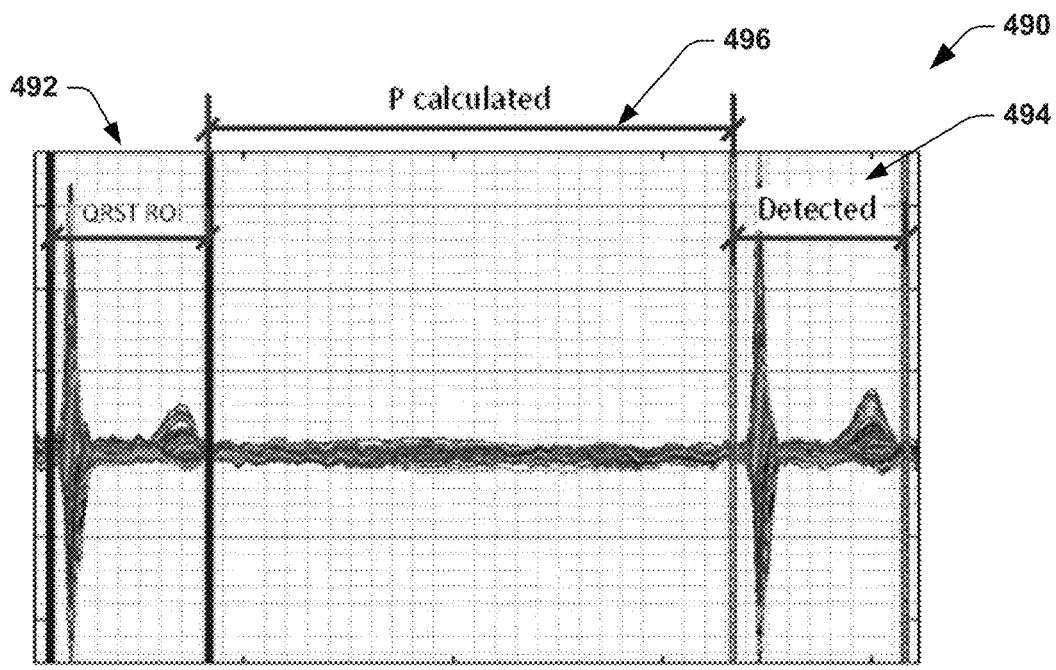
FIG. 23 depicts an example of a plurality of waveforms demonstrating identification of a P-wave based on a QRST template region.

As an example, a QRST complex can be defined to generate one template ROI, such as shown in the plot 490 of ECG data in FIG. 23. For example, a QRST template 492 is calculated and a matching ROI is detected via correlation, as described above. A P wave can be automatically calculated as between two adjacent ROIs, as shown in FIG. 23. As a result of using a single template for the entire QRST complex, a single set of calipers can be used to identify a region of interest.

Figure 24:
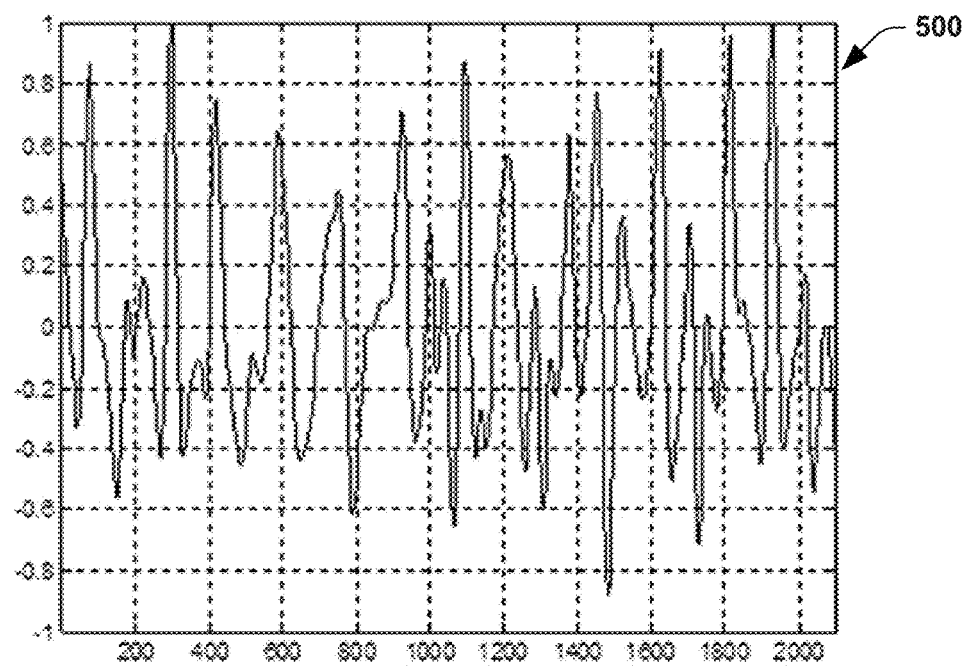
FIG. 24 depicts an example of a correlation plot of a QRS template.
Figure 25:
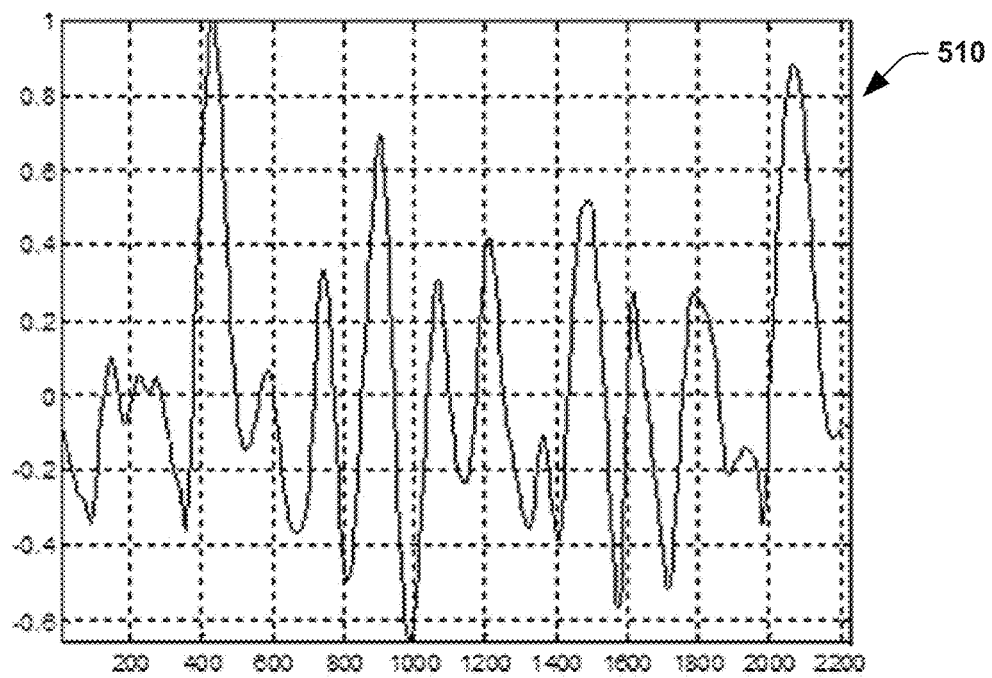
FIG. 25 depicts an example of a correlation plot of a T template.
Figure 26:
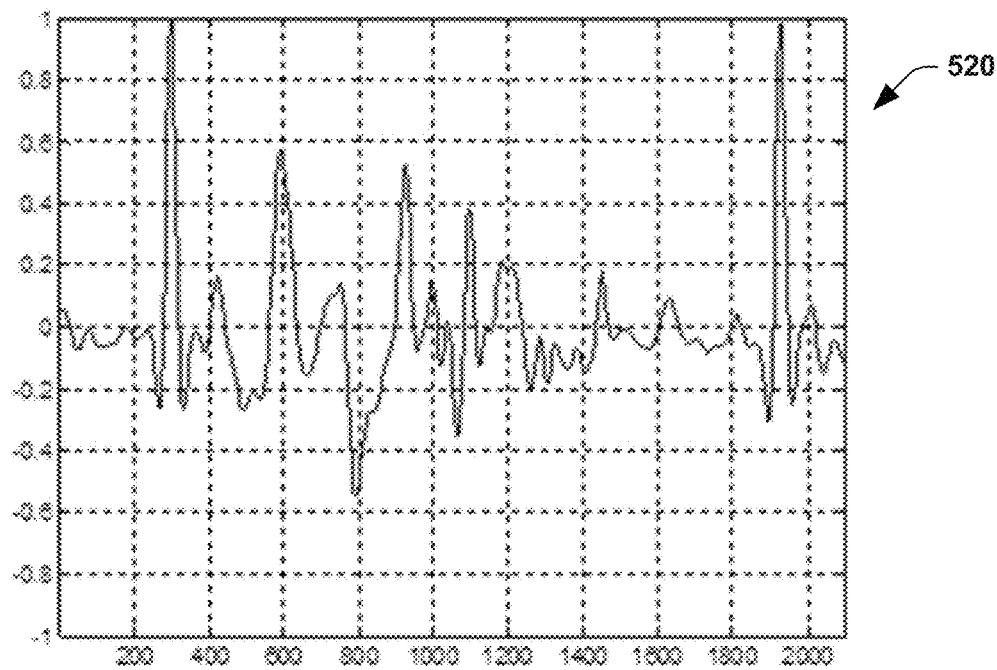
FIG. 26 demonstrates an example of a correlation plot of a QRST template.

FIGS. 24, 25 and 26 depict different correlation plots 500, 510 and 520 demonstrating resulting differences from using different types of templates. For instance, FIG. 24 depicts an example of a correlation plot 500 of a QRS template. FIG. 25 depicts an example of a correlation plot 510 of a T template. FIG. 26 demonstrates an example of a correlation plot 520 of a composite QRST template. Thus, the single QRST template reduces the requisite processing (compared to using separate QRS and T templates individually) and can reduce the amount of user interaction compared to some existing approaches.

As a simplified example, QRST detection and removal can define the QRST complex once per interval manually in response to user input. In another example, the QRST detection and removal function can implement a semi-automatic or fully automatic approach, such by automatic template matching with some standard QRST complex or a pre-selected or even pre-detected QRST.

QRST Removal

The QRST detection and removal function (e.g., function 32, 480, 578) operates to remove QRS and T signals so that the residual signal magnitude in the QRS and T regions is not superior to that of P wave or causing residual signal within the P wave. To reduce artifacts caused by QRS and T signals on P signals during later filtering to obtain the interesting frequency bandwidth (e.g., about 4-12 Hz), QRST detection and removal can remove the QRS\T regions by interpolating with low frequency signals. This can be achieved by using approaches like monotonic cubic spline interpolation between the beginning and end of each of the QRST ROIs.

Figure 27:
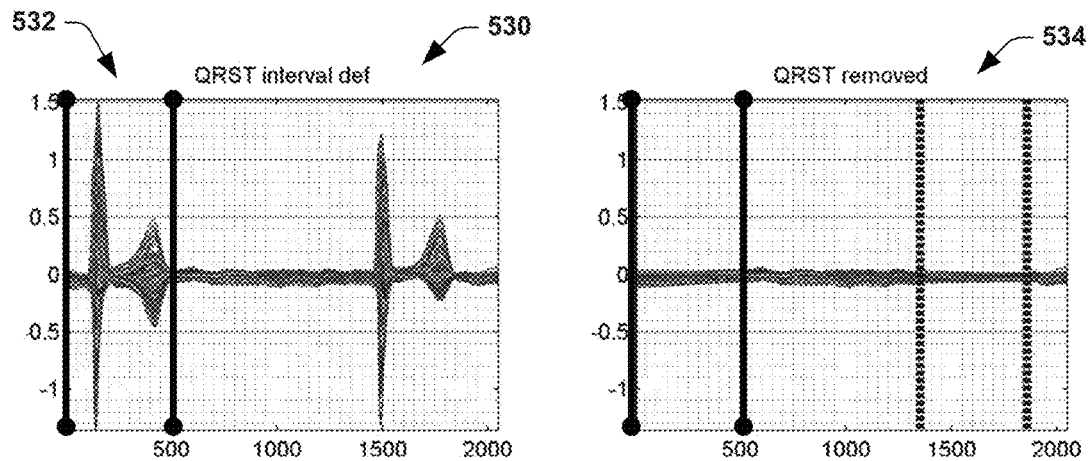
FIG. 27 demonstrates plots of a QRST interval definition and resulting waveform after removing QRST portions.
Figure 28:
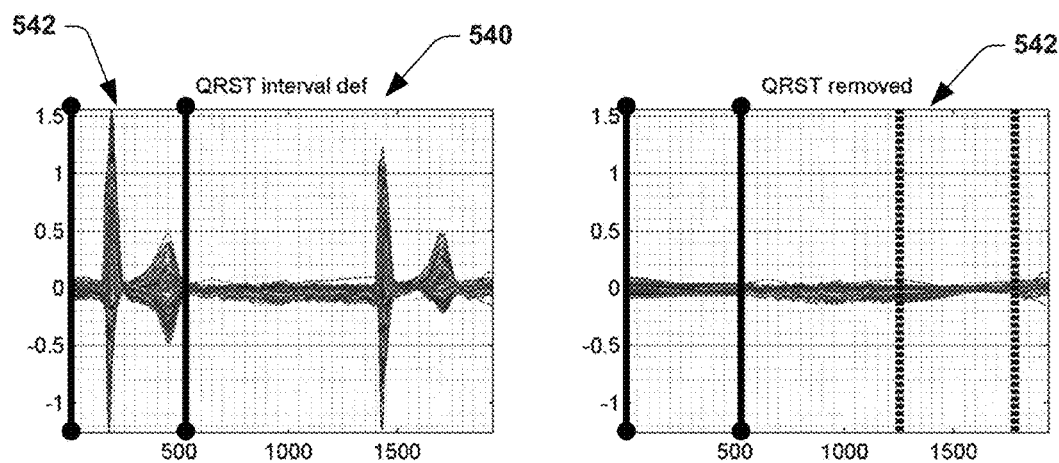
FIG. 28 demonstrates another example of a QRST interval definition and resulting waveform after QRST removal.

FIGS. 27 and 28 demonstrate two example cases where existing QRS+T subtraction removal approach failed at detection, but the approach disclosed herein succeeded at detection and removal of the QRST. In the left plots 530 and 540 of FIGS. 27 and 28, a QRST template is defined for an interval, indicated at 532 and 542, respectively. In the right plots 534 and 544 of FIGS. 27 and 28, the QRST is removed.

As another approach, instead of defining QRST complex and performing template matching, the QRST detection and removal function can simply define the P wave for one beat, and then any signal outside of the P wave will be padded. This approach can work in a beat by beat manual framework, for example.

Atrial Signals in QRST Complex

For a normal heart in sinus rhythm, there is no underlying atrial signal in the QRST complex. However, for arrhythmias like AF (atrial fibrillation), atrial signals may present during the QRST complex. To use atria signals during the QRST complex, a reliable QRST subtraction approach, such as disclosed herein is desirable to remove the ventricular portion of the signals to enable analysis of the atrial signals.

One example to mitigate corruption of atrial signals with in a region of interest (QRST) is to identify a good QRST complex during a normal sinus rhythm, with or without signal average (e.g., a "clean" QRST complex). The QRST detection and removal function can perform template matching between the clean QRST complex and the QRST complex in AF. By not performing any ROI averaging in the process of defining the template, the QRST detection and removal function can subtract the contribution of the clean QRST complex from each arrhythmogenic QRST complex, such that the remaining signal within the QRST interval would include atrial signals.

To reduce user interaction during map creation, the user can pick one template per study. For example, to define a QRST complex, the beginning and ending of the interval definition are placed at a location where signals are flat or when the heart has less activity. As baseline drift due to respiratory motion etc. can change the template profile, the baseline removal step can be performed before QRST removal. The baseline removal can also be before automatic bad-channel identification to reduce baseline drift impact on that part of the overall process.

By way of further example, the QRST detection and removal process may be implemented as a method. The method includes performing principal component analysis on a selected region of interest with respect to a plurality of electrograms to define a QRST template. The method also includes correlating the QRST template relative to an interval of each of the plurality of electrograms to identify matching regions of interest. The method also includes removing the identified matching regions of interest from each of the plurality of electrograms using interpolation.

For example, the region of interest is selected manually in response to a user input or the region of interest is selected automatically.

As another example, the QRST template defines a single template applied to each of the electrograms in a given time interval.

As another example, the interpolation implemented by the method includes monotonic cubic spline interpolation to connect P waves together for adjacent beats.

As another example, prior to removing the identified matching regions of interest, the method further includes averaging the template across the regions of interest.

As another example, prior to removing the identified matching regions of interest, the method further includes adjusting the template to account for baseline drift in the electrograms.

As another example, the electrograms include a time interval exhibiting atrial fibrillation. In this example, the method further includes:
  identifying a clean QRST complex during a sinus rhythm without the atrial fibrillation;
  performing template matching between the clean QRST complex and a QRST complex during the atrial fibrillation; and
  removing the clean QRST template from the electrograms.

In some examples, the method further includes automatically determining each P wave as a region between two adjacent QRST regions of interest.

As another example, the method further includes detecting R-peaks for each of the electrograms and using the detected R-peaks to locate an interval containing QRST complexes.

As disclosed, one or more non-transitory computer-readable media stores instructions to perform any variation of the method of QRST detection and removal.

Acquisition, Output Displays and Treatment

Figure 29:
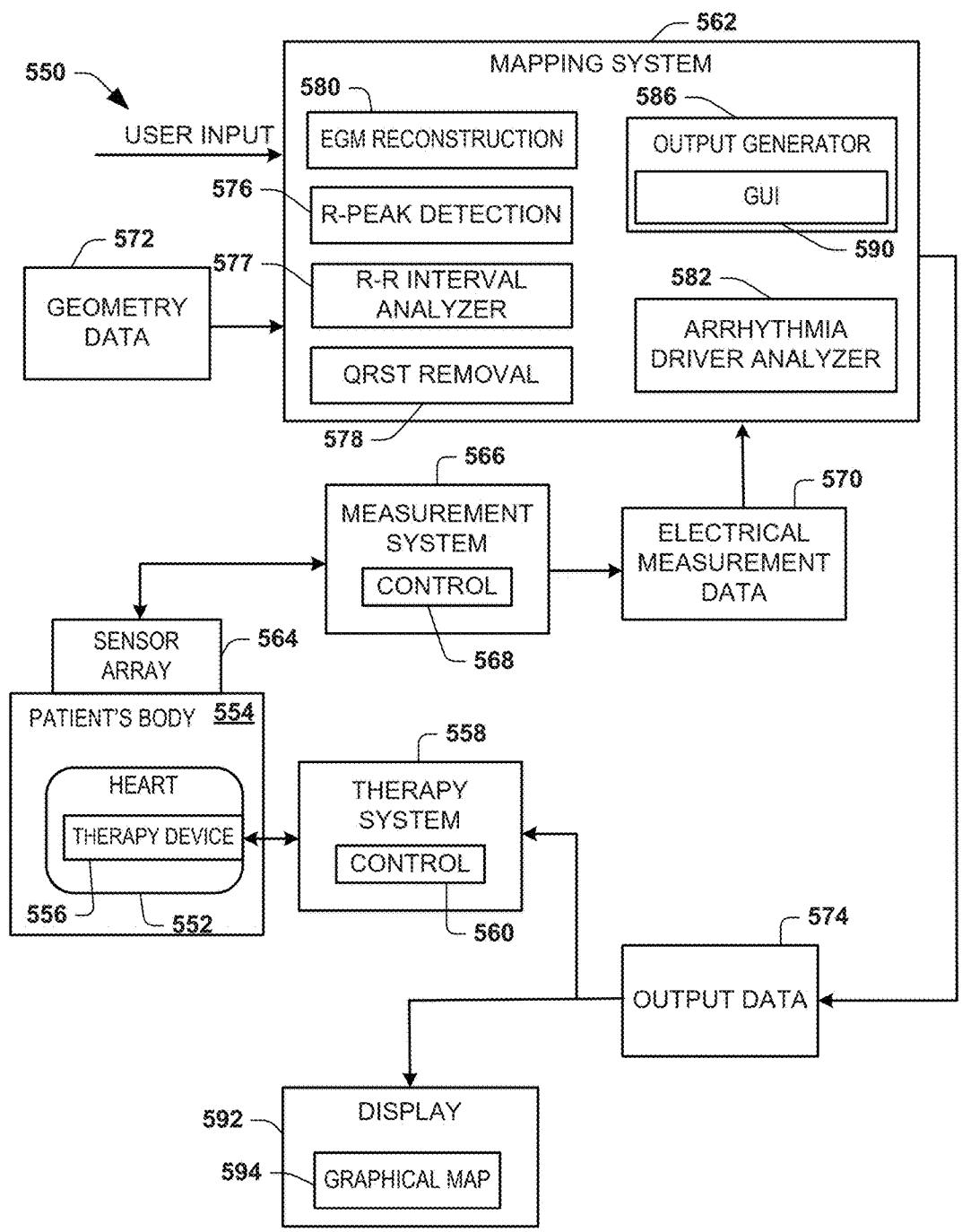
FIG. 29 depicts an example of a system that can be utilized to perform diagnostics and/or treatment.

FIG. 29 depicts an example of a system 550 that can be utilized for generating an output to process body surface signals to characterize arrhythmogenic activity of a patient. In some examples, the system 550 can generate a graphical map (e.g., a body surface map or a map on a heart model) 594 and/or display processed electrical signals. The system can also provide information in other formats to provide guidance to the user indicative of one or more of computed signal characteristics as well as information derived from such computed signal characteristics.

As disclosed herein, the system 550 has applications throughout various phases of patient care. As an example, the system can be used as part of a patient screening process (e.g., as part of a diagnostic and/or treatment planning procedure) or to perform post-treatment evaluation. Additionally, the system 550 can be utilized as part of a treatment procedure, such as to determine parameters for delivering a therapy to the patient (e.g., delivery location, amount and type of therapy). For example, a catheter, having one or more therapy delivery devices 556 affixed thereto can be inserted into the body 554 as to contact the patient's heart 552, endocardially or epicardially. Those skilled in the art will understand and appreciate various types and configurations of therapy delivery devices 556 that can be utilized, which can vary depending on the type of treatment and the procedure. For instance, the therapy device 556 can be configured to deliver electrical therapy, chemical therapy, sound wave therapy, thermal therapy or any combination thereof.

By way of further example, the therapy delivery device 556 can include one or more electrodes located at a tip of an ablation catheter configured to generate heat for ablating tissue in response to electrical signals (e.g., radiofrequency energy) supplied by a therapy system 558. In other examples, the therapy delivery device 556 can be configured to deliver cooling to perform ablation (e.g., cryogenic ablation), to deliver chemicals (e.g., drugs), ultrasound ablation, high-frequency radio frequency ablation, or a combination thereof. In still other examples, the therapy delivery device 556 can include one or more electrodes located at a tip of a pacing catheter to deliver electrical stimulation, such as for pacing the heart, in response to electrical signals (e.g., pacing current pulses) supplied by a therapy system 558. Other types of therapy can also be delivered via the therapy system 558 and the invasive therapy delivery device 556 that is positioned within the body.

As a further example, the therapy system 558 can be located external to the patient's body 554 and be configured to control therapy that is being delivered by the device 556. For instance, the therapy system 558 includes controls (e.g., hardware and/or software) 560 that can communicate (e.g., supply) electrical signals via a conductive link electrically connected between the delivery device (e.g., one or more electrodes) 556 and the therapy system 558. The control system 560 can control parameters of the signals supplied to the device 556 (e.g., current, voltage, repetition rate, trigger delay, sensing trigger amplitude) for delivering therapy (e.g., ablation or stimulation) via the electrode(s) 554 to one or more location of the heart 552. The control circuitry 560 can set the therapy parameters and apply stimulation based on automatic, manual (e.g., user input) or a combination of automatic and manual (e.g., semiautomatic controls). One or more sensors (not shown) can also communicate sensor information back to the therapy system 558. The position of the device 556 relative to the heart 552 can be determined and tracked intraoperatively via an imaging modality (e.g., fluoroscopy, x-ray), a mapping system 562, direct vision or the like. The location of the device 556 and the therapy parameters thus can be combined to determine corresponding therapy delivery parameter.

Before, during and/or after providing a therapy via the therapy system 558, another system or subsystem can be utilized to acquire electrophysiology information for the patient. In the example of FIG. 29, a sensor array 564 includes one or more body surface electrodes that can be utilized for measuring patient electrical activity. As one example, the sensor array 564 can correspond to a high-density arrangement of body surface sensors (e.g., greater than approximately 200 electrodes) that are distributed over a portion of the patient's torso (e.g., thorax) for measuring electrical activity associated with the patient's heart (e.g., as part of an electrocardiographic mapping procedure). An example of a high-density body surface non-invasive apparatus that can be used as the sensor array 564 is shown and described in International Application No. PCT/US2009/063803, filed 10 Nov. 2009. Other arrangements and numbers of sensing electrodes can be used as the sensor array 564. For example, the array can be a reduced set of electrodes, which does not cover the patient's entire torso and is designed for measuring electrical activity for a particular purpose (e.g., an array of electrodes specially designed for analyzing AF and/or VF) and/or for monitoring a predetermined spatial region of the heart. In other examples, an array having a traditional or modified 12-lead ECG or a single electrode can be implemented as the sensor array 564 to provide body surface electrical signals.

In some examples, one or more sensors may also be located on the device 556 that is inserted into the patient's body. Such sensors can be utilized separately or in conjunction with the non-invasive sensor array 564 for mapping electrical activity for an endocardial surface, such as the wall of a heart chamber, as well as for an epicardial surface. Additionally, such electrode can also be utilized to help localize the device 556 within the heart 552, which can be registered into an image or map that is generated by the system 550. Alternatively, such localization can be implemented in the absence of emitting a signal from an electrode within or on the heart 552.

In each of such example approaches for acquiring patient electrical information, including invasively, non-invasively, or a combination of invasive and non-invasive sensing, the sensor array(s) 564 provide the sensed electrical information to a corresponding measurement system 566. The measurement system 566 can include appropriate controls 568 for providing electrical measurement data 570 that describes electrical activity (e.g., electrograms) detected by the sensors in the sensor array 564. For example, signal processing circuitry of the measurement system 566 can convert the signal(s) to corresponding digital information. The measurement system 566 can further process the digital information corresponding to one or more electrophysiological signals from sensor array 564 and remove non-arrhythmogenic characteristics from each such signal and to provide preprocessed data that is stored in memory as the electrical measurement data 570.

The control 568 can also be configured to control the data acquisition process for measuring electrical activity and providing the measurement data 570 (e.g., at a predefined sample rate). In some examples, the control 568 can control acquisition of measurement data 570 separately from operation of the therapy system 558 (if implemented), such as in response to a user input. In other examples, the measurement data 570 can be acquired concurrently with and in synchronization with delivering therapy by the therapy system, such as to detect electrical activity of the heart 552 that occurs in response to applying a given therapy (e.g., according to therapy parameters). For instance, appropriate time stamps can be utilized for indexing the temporal relationship between the respective measurement data 570 and therapy parameters use to deliver therapy as to facilitate the evaluation and analysis thereof.

The mapping system 562 is programmed to combine the measurement data 570 corresponding to sensed body surface electrical activity of the heart 552 to provide corresponding output data 574. The output data 574 can be represent or characterize detected electrograms on the body surface and/or within the heart. The output data can also represent information derived from the measured signals, such as disclosed herein.

As one example, the mapping system 562 includes an R-peak detection function 576, such as corresponding to R-peak detector 20 (e.g., as disclosed herein with respect to FIGS. 1-21). The mapping system 562 can also include a QRST detection and removal function 578, such as corresponding to QRST detection and removal function 32 (e.g., as disclosed with respect to FIG. 1 and FIGS. 22-28). Each of the functions 576 and 578 can be applied to electrogram data, demonstrated as electrical measurement data 570. As mentioned, in some examples, the R-peak detection function 576 and QRST detection and removal function 578 operate on raw electrogram data (acquired via non-invasive and/or invasive electrodes to measure electrograms across a body surface) to determine R-peak locations and remove QRST signals from the raw signals, respectively.

As a further example, R-peak detection function 576 is programmed to compute an R-R interval from the stored R-peak location data (R-peaks), and based on the identifying adjacent R-peaks suggest one or more heart beats based on the computed R-R interval relative to suggestion criteria. For example, the suggestion criteria include at least one of default or configurable time values. The suggestion criteria includes a threshold that is set to a fractional portion of a specified R-Peak to R-Peak length, wherein the suggestion criteria is applied to a plurality of computed R-R intervals for at least some of the plurality of electrograms.

The mapping system 562 includes an output generator to provide the output data 574 to visualize on a display 592 one or more intervals of electrograms based on the electrical measurement data acquired for the patient over one or more time intervals (e.g., before, after or during a study or treatment procedure). In an example where the sensor array 564 includes a plurality of electrodes, the output data 574 can include a selected set of channels for electrograms measured via sensors 564 on the patient's body surface. Parameters can be set to identify a subset of signals meeting one or more user configurable parameters (e.g., via GUI 590). Some examples of output displays that can be provided by the output generator 586 are disclosed with respect to FIGS. 30 and 31. The output generator thus generates the output data to display a graphical representation of electrical activity (an arrangement of electrograms) for the suggested one or more beats, that have been determined as disclosed herein.

In some examples, computed data can be mapped to a geometric surface of a heart model. As disclosed herein, the maps can be computed based on electrical data that is acquired non-invasively via one or more electrodes in the sensor array 564 distributed on the surface of the patient's body 554.

Since the measurement system 566 can measure electrical activity of a predetermined region or the entire heart concurrently (e.g., where the sensor array 564 including a plurality of electrodes covering the entire thorax of the patient's body 554), the resulting output data (e.g., electrograms and/or electrocardiographic maps) thus can also represent concurrent data for the predetermined region or the entire heart in a temporally and spatially consistent manner. The time interval for which the output data/maps are computed can be selected based on user input. Additionally or alternatively, the selected intervals can be synchronized with the application of therapy by the therapy system 558. As disclosed herein, the indication of the presence or absence of stable arrhythmogenic activity can be computed from the body surface electrical signal(s) in the absence of performing electrogram reconstruction based on patient geometry.

In other examples, where additional information may be available and geometry data 572 can be obtained, the system may include electrogram reconstruction 580 programmed to compute an inverse solution and provide corresponding reconstructed electrograms based on the process signals and the geometry data 572. For example, the geometry data 572 can correspond to a mathematical model, such as can be a generic model or a model that has been constructed based on image data obtained for the patient (e.g., via an imaging modality, such as CT, MRI, bi-plane x-ray or the like) and provides spatial coordinates for the patient's heart 552 and electrodes on the sensor array. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 550 include those disclosed in U.S. Pat. Nos. 7,983,743 and 6,772,004. The EGM reconstruction 580 thus can reconstruct the body surface electrical activity measured via the sensor array 564 onto a multitude of locations on a cardiac envelope (e.g., greater than 1000 locations, such as about 2000 locations or more). In other examples, the mapping system 562 can compute electrical activity over a sub-region of the heart based on electrical activity measured invasively, such as via a basket catheter or other form of measurement probe (e.g., on or attached to device 556).

Additionally, the mapping system 562 can include an arrhythmia driver analyzer 582 to compute an indication of arrhythmogenic activity (e.g., driver activity, such as rotors and focal) based on analysis of cardiac electrical activity, which can be measured directly or reconstructed to a cardiac envelope. For instance, the reconstructed electrical activity can be computed to a cardiac envelope by solving the inverse problem based on non-invasively measured body surface electrical activity (e.g., electrograms) and the geometry data 572. The driver activity on the cardiac envelope can be used to confirm the detected stable driver activity that is determined by the signal processor 52 based on analysis only of one or more body surface signals (without geometry data). Additionally or alternatively, the driver activity on the cardiac envelope can be used to more particularly identify one or more spatial locations on the heart associated with the driver activity. The spatial locations on the heart thus can be used to identify one or more treatment sites for positioning the therapy device to deliver treatment to the patient's heart 552.

Parameters associated with the graphical representation, corresponding to an output visualization of the computed map, such as including selecting a time interval, a type of information that is to be presented in the visualization and the like can be selected in response to a user input via a corresponding visualization GUI 590.

Additionally, the output data 574 can be utilized by the therapy system 558, if included in the system 550. The control that is implemented can be fully automated control, semi-automated control (partially automated and responsive to a user input) or manual control based on the output data 574. In some examples, the control 560 of the therapy system can utilize the output data to control one or more therapy parameters. As an example, the control 560 can control delivery of ablation therapy to a site of the heart (e.g., epicardial or endocardial wall) based on arrhythmogenicity that has been determined by the function 582. For instance, the delivery of therapy can be terminated automatically in response to detecting the absence of stable driver activity. In other examples, an individual can view the map generated in the display to manually control the therapy system based on information that is visualized. Other types of therapy and devices can also be controlled based on the output data.

Figure 30:
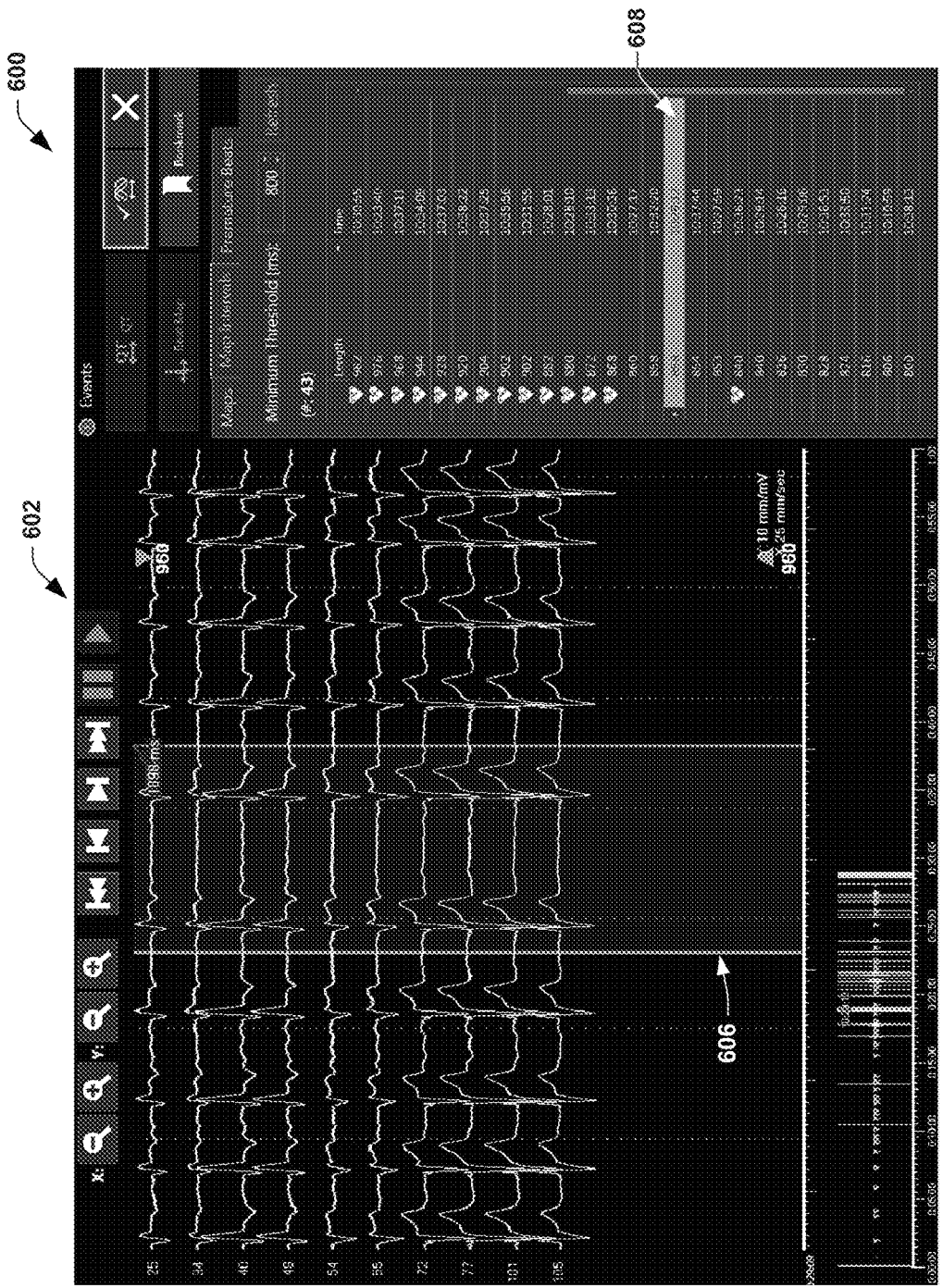
FIG. 30 depicts an example of a graphical user interface that can be utilized to visualize selected portions of waveforms for analysis.
Figure 31:
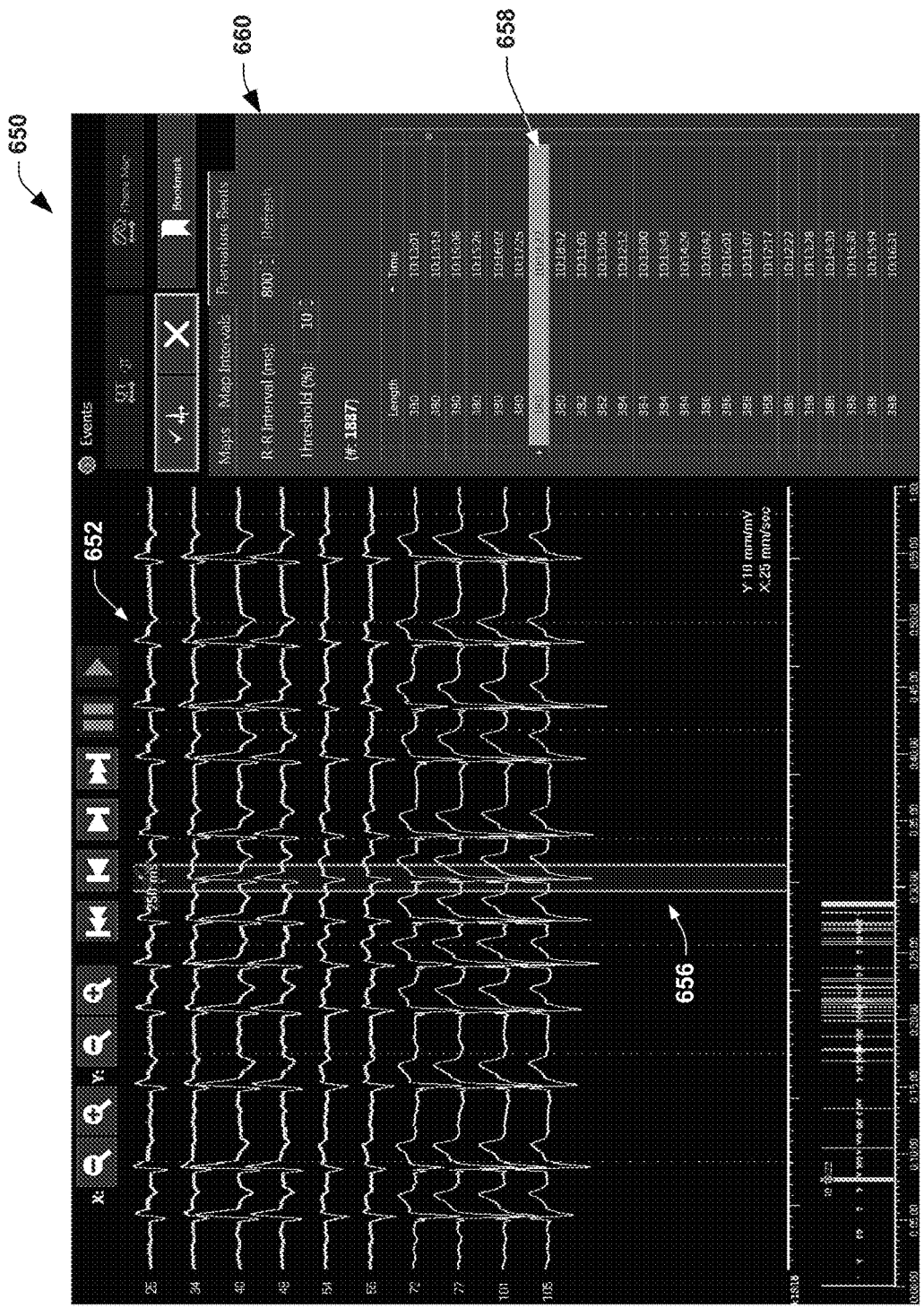
FIG. 31 depicts another example of graphical user interface that can be utilized to visualize selected portions of waveforms for analysis.

FIGS. 30 and 31 demonstrate examples of output maps that can be generated, showing electrograms and GUI controls to enable user interaction, such as to set parameters and select signals for display. Cardiac mapping for phase analysis requires a long beat for computation, whereas mapping an ectopic or premature beat (a short beat) for traditional mapping also adds value to the electrophysiology (EP) workflow. The output generator 586 includes a function for suggesting beats automatically to the user, which is applicable to both phase mapping and traditional beat-based cardiac mapping.

The output generator 586 suggests beats based on the R-peak detection 576 that provides locations in time of R-peaks within each QRST complex in a heartbeat across all channel, for example. The output generator 586 can specify beats as the interval between adjacent R-peaks.

For phase mapping suggested beats, the output generator 586 automatically detects beats and suggests them to the user for mapping via the interactive output. The output generator 586 can analyze the electrograms and control the display based on some or all of the following beat suggestion criteria:
 a. beats are longer from R-peak to R-peak than a predetermined threshold, which can be a default (e.g., about 1200 ms) or user programmable (e.g., in response to a user input);
 b. beats are shorter than a threshold of R-peak to R-peak minus a defined QT-length, which can be a default value (e.g., >850 ms) or user programmable in response to a user input; and/or
 c. beats are shorter than a system-configured maximum duration, which can be a default value (e.g., about 10 sec) or user programmable (e.g., in response to a user input).

For the example of traditional beat mapping suggested beats, the output generator 586 can analyze the electrograms and control the display based on some or all of the following beat suggestion criteria:
 a. an R-Peak to R-peak length that is less than a percentage threshold. The threshold can be a default (e.g., about 10%) or user programmable fractional value, with respect to a baseline R-peak to R-peak length in ms, which can be a default (e.g. 800 ms) or be user programmable.

In view of the foregoing, the mapping system 562 thus enables the user to view suggested beats in a single list (e.g., right side column in FIGS. 30 and 31), and select them for fast review and then creation of maps, without requiring constant attention to live data acquisition to find mapping beats manually. In some cases, beat detection may be disabled (e.g., in response to user input) during periods of non-clinical interest (for example, pacing, or during procedure setup), and these beats are filtered from the list. Suggested beats may also be ignored after user review, which also filters those out of the list.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on."

What is claimed is:

1. A method, comprising:
performing, with one or more computer processors, amplitude-based detection to determine locations of amplitude R-peaks for a plurality of electrograms based on exceeding an amplitude cutoff, each of the plurality of electrograms corresponding to a respective input channel;
performing, with the one or more computer processors, wavelet-based detection to determine locations of wavelet R-peaks for the plurality of electrograms;
adjusting, with the one or more computer processors, the locations of wavelet R-peaks, to provide adjusted R-peak locations placed at consistent locations relative to QRS complex morphology for respective electrograms based on the locations of amplitude R-peaks;
storing, in memory communicatively coupled to the one or more computer processors, R-peak location data to specify the adjusted R-peak locations for the plurality of electrograms based on the adjusting; and
driving an output to a display to visualize an output based on the R-peak location data.

2. The method of claim 1, further comprising computing an R-R interval from the stored R-peak location data.

3. The method of claim 2, further comprising suggesting one or more beats based on the computed R-R interval relative to suggestion criteria.

4. The method of claim 3, wherein the suggestion criteria include at least one of default or configurable time values, and
wherein the suggestion criteria includes a threshold that is set to a fractional portion of a specified R-peak to R-peak length, wherein the suggestion criteria is applied to a plurality of computed R-R intervals for at least some of the plurality of electrograms.

5. The method of claim 3, further comprising generating output data to display a graphical representation of electrical activity for the suggested one or more beats, the graphical representation of electrical activity comprising a portion of the plurality of electrograms for the suggested one or more beats and/or a graphical map derived from the plurality of electrograms for the suggested one or more beats.

6. The method of claim 1, wherein performing amplitude-based detection further comprises:
reducing baseline drift from the plurality of electrograms to provide baseline-reduced electrograms; and
detecting the R-peak amplitude from the baseline-reduced electrograms.

7. The method of claim 1, wherein performing amplitude-based detection further comprises:
constructing a histogram of amplitude peak locations from the plurality of electrograms; and
analyzing at least one of the peaks in the histogram to determine the amplitude cutoff.

8. The method of claim 1, wherein performing wavelet-based detection further comprises:
employing a multi-tree complex wavelet transform to detect the wavelet R-peaks; and
determining the wavelet R-peaks based on the wavelet detections.

9. The method of claim 8, wherein performing the wavelet-based R-peak detection further comprises using a moving average filter of a predetermined length to distinguish noise from the detected wavelet R-peaks.

10. The method of claim 1, wherein adjusting locations further comprises:
identifying wavelet-based R-peak detections that do not have corresponding amplitude detections; and
verifying the wavelet-based R-peak detections based on evaluation of a refractory period between peaks and the detected peaks at neighboring nodes.

11. The method of claim 1, wherein adjusting locations further comprises:
implementing a windowing method by evaluating the detected R-peaks in overlapping regions of successive windowed segments to identify missed R-peaks and remove duplicate detected R-peaks.

12. The method of claim 1, further comprising:
using the R-peak location data to select a region of interest containing a QRST complex;
performing principal component analysis on the selected region of interest with respect to the plurality of electrograms to define a QRST template;
correlating the QRST template relative to an interval of each of the plurality of electrograms to identify matching regions of interest; and
removing the identified matching regions of interest from each of the plurality of electrograms using interpolation.

13. The method of claim 1, further comprising measuring a plurality of electrical signals from a plurality of sensors at a plurality of measurement locations to provide the plurality of electrograms, the measurement locations being invasive or non-invasive with respect to a patient's body.

14. A system comprising:
a non-transitory memory to store electrical data representing a plurality of electrograms and machine-readable instructions; and
a processor to access the non-transitory memory and execute the machine-readable instructions, the instructions comprising:
amplitude peak detection code programmed to perform amplitude-based detection to determine locations of amplitude R-peaks for a plurality of electrograms based on amplitude cutoff, each of the plurality of electrograms corresponding to a respective input channel;
wavelet peak detection code programmed to perform wavelet-based detection to determine locations of wavelet R-peaks for the plurality of electrograms;
location adjustment code programmed to adjust locations of wavelet R-peaks to provide adjusted R-peak locations placed at consistent locations relative to QRS complex morphology for respective electrograms based on the locations of amplitude R-peaks; and
code programmed to store in the memory R-peak location data to specify the adjusted R-peak locations for the plurality of electrograms based on the adjusting; and
a display to visualize a graphical representation based on the R-peak location data.

15. The system of claim 14, further comprising a measurement device comprising a plurality of sensors to measure electrical signals from a plurality of spatial locations across a body surface to provide the plurality of electrograms, the spatial locations being invasive or non-invasive with respect to a patient's body.

16. The system of claim 14, wherein the instructions further comprise R-R interval calculator code to compute the R-R interval lengths based on the R-peak location data.

17. The system of claim 16, wherein the R-R interval calculator code is further programmed to suggest one or more beats based on the computed R-R interval relative to suggestion criteria, and
wherein the suggestion criteria includes a threshold that is set to a fractional portion of a specified R-peak to R-peak length, the suggestion criteria being applied to a plurality of computed R-R intervals for at least some of the plurality of electrograms.

18. The system of claim 16, wherein the graphical representation comprises a visualization of the plurality of electrograms for the suggested one or more beats and/or a graphical map derived from the plurality of electrograms for the suggested one or more beats.

19. The system of claim 14, wherein the instructions further comprise baseline removal code programmed to reduce baseline drift from the plurality of electrograms to provide baseline-reduced electrograms, wherein the R-peak amplitude is detected from the baseline-reduced electrograms.

20. The system of claim 14, wherein the amplitude peak detection code further comprises instruction for:
constructing a histogram of amplitude peak locations from the plurality of electrograms; and
analyzing at least one of the peaks in the histogram to determine the amplitude cutoff.

21. The system of claim 14, wherein the wavelet peak detection code further comprises instructions for:
employing a multi-tree complex wavelet transform to detect the wavelet R-peaks;
determining the wavelet R-peaks based on the wavelet detections.

22. The system of claim 14, wherein the location adjustment code further comprises instructions for:
identifying wavelet-based R-peak detections that do not have corresponding amplitude detections; and
verifying the wavelet-based R-peak detections based on evaluation of a refractory period between R-peaks and the detected R-peaks at neighboring nodes.

23. The system of claim 14, further comprising:
using the R-peak location data to select a region of interest containing a QRST complex;
performing principal component analysis on the selected region of interest with respect to the plurality of electrograms to define a QRST template;
correlating the QRST template relative to an interval of each of the plurality of electrograms to identify matching regions of interest; and
removing the identified matching regions of interest from each of the using interpolation.

* * * * *